(12) United States Patent
Dweik et al.

(10) Patent No.: US 11,723,553 B2
(45) Date of Patent: Aug. 15, 2023

(54) METHOD AND SYSTEM FOR DETECTION AND/OR QUANTIFICATION OF DELTA-9-TETRAHYDROCANNABINOL IN EXHALED BREATH

(71) Applicant: Giner, Inc., Newton, MA (US)

(72) Inventors: Badawi M. Dweik, Foxborough, MA (US); Avni A. Argun, Newton, MA (US); Anahita Karimi, Westwood, MA (US)

(73) Assignee: GINER, INC., Newton, MA (US)

( * ) Notice: Subject to any disclaimer, the term of this patent is extended or adjusted under 35 U.S.C. 154(b) by 391 days.

(21) Appl. No.: 16/788,035

(22) Filed: Feb. 11, 2020

(65) Prior Publication Data

US 2020/0397340 A1 Dec. 24, 2020

Related U.S. Application Data

(60) Provisional application No. 62/803,764, filed on Feb. 11, 2019.

(51) Int. Cl.
*A61B 5/097* (2006.01)
*G01N 27/327* (2006.01)
(Continued)

(52) U.S. Cl.
CPC ............ *A61B 5/082* (2013.01); *A61B 5/18* (2013.01); *A61K 31/352* (2013.01);
(Continued)

(58) Field of Classification Search
CPC ........ A61B 5/082; A61B 5/18; A61K 31/352; G01N 27/308; G01N 27/327; G01N 27/3335
See application file for complete search history.

(56) References Cited

U.S. PATENT DOCUMENTS 4,841,905 A * 6/1989 Scholefield ...... G01N 35/00009
118/404
4,871,439 A * 10/1989 Enzer ................. G01N 27/4165
204/411

(Continued)

FOREIGN PATENT DOCUMENTS

CN 100364126 C 1/2008
WO 2007136523 A2 11/2007
(Continued)

OTHER PUBLICATIONS

Balbino et al., "Electrochemical Study of Delta-9-Tetrahydrocannabinol by Cyclic Voltammetry Using Screen Printed Electrodes, Improvements in Forensic Analysis," Sensors and Transducers, vol. 207, Issue 12, Dec. 2016, pp. 73-78 (Year: 2016).*

(Continued)

*Primary Examiner* — Alexander S Noguerola
(74) *Attorney, Agent, or Firm* — Kriegsman & Kriegsman

(57) ABSTRACT

Method and system for detecting and/or quantifying $\Delta^9$-tetrahydrocannibinol (THC) in exhaled breath. In one embodiment, the method involves providing an electrochemical sensing element, the electrochemical sensing element including a working electrode, and also providing a filter that traps THC in exhaled breath. Next, a subject exhales onto the filter, whereby at least some of the THC, if present, is trapped in the filter. Next, the filter is washed with an eluent, whereby at least some of the THC trapped in the filter is eluted in an eluate. Next, the eluate is deposited onto the working electrode of the electrochemical sensing element, and the eluate is dried, whereby any THC present is immobilized on the working electrode. Next, an electrolytic solution is delivered to the electrochemical sensing element, and the THC immobilized on the working electrode is directly electrochemically detected and/or quantified using a (Continued)

pulse voltammetry technique, such as square-wave voltammetry.

25 Claims, 28 Drawing Sheets

(51) Int. Cl.
| | | |
|---|---|---|
| | *A61B 5/08* | (2006.01) |
| | *A61B 5/18* | (2006.01) |
| | *A61K 31/352* | (2006.01) |
| | *G01N 27/30* | (2006.01) |
| | *G01N 27/333* | (2006.01) |

(52) U.S. Cl.
CPC ......... *G01N 27/308* (2013.01); *G01N 27/327* (2013.01); *G01N 27/3335* (2013.01)

(56) References Cited

U.S. PATENT DOCUMENTS

| | | | |
|---|---|---|---|
| 5,520,787 A * | 5/1996 | Hanagan | C12Q 1/001 435/287.7 |
| 5,837,546 A | 11/1998 | Allen et al. | |
| 6,134,945 A * | 10/2000 | Gerstel | G01N 30/12 422/78 |
| 6,531,702 B1 * | 3/2003 | Mischler | B01L 3/502746 250/339.12 |
| 7,790,400 B2 | 9/2010 | Jehanli et al. | |
| 8,877,038 B2 | 11/2014 | Kampouris et al. | |
| 9,011,657 B2 | 4/2015 | Parselle et al. | |
| 9,429,564 B2 | 8/2016 | Beck | |
| 9,709,581 B1 | 7/2017 | Gordon et al. | |
| 11,026,596 B1 * | 6/2021 | Lynn | A61B 5/087 |
| 2008/0020477 A1 | 1/2008 | Pronovost | |
| 2009/0294298 A1 | 12/2009 | Compton et al. | |
| 2010/0031757 A1 * | 2/2010 | Hoyer | G01N 1/2813 73/863.01 |
| 2010/0081189 A1 * | 4/2010 | Zantl | B01L 3/502715 422/82.01 |
| 2011/0143961 A1 | 6/2011 | Lednev et al. | |
| 2012/0132524 A1 | 5/2012 | Parselle et al. | |
| 2013/0168175 A1 | 7/2013 | Polzius et al. | |
| 2013/0334045 A1 | 12/2013 | Kuhr et al. | |
| 2014/0151224 A1 * | 6/2014 | Glezer | B01L 9/527 204/407 |
| 2014/0273187 A1 | 9/2014 | Johnson et al. | |
| 2014/0288454 A1 | 9/2014 | Paz et al. | |
| 2014/0313322 A1 | 10/2014 | Denise | |
| 2015/0033824 A1 | 2/2015 | Hammarlund et al. | |
| 2015/0305651 A1 | 10/2015 | Attariwala et al. | |
| 2017/0008000 A1 | 1/2017 | Kim | |
| 2017/0030882 A1 | 2/2017 | Skoda | |
| 2017/0036207 A1 | 2/2017 | Wright et al. | |
| 2017/0336389 A1 | 11/2017 | Trexler et al. | |
| 2018/0306775 A1 | 10/2018 | Beck et al. | |
| 2020/0400695 A1 | 12/2020 | Dweik et al. | |

FOREIGN PATENT DOCUMENTS

| | | |
|---|---|---|
| WO | 2009081153 A2 | 7/2009 |
| WO | 2012120140 A1 | 9/2012 |
| WO | 2017147687 A2 | 9/2017 |
| WO | 2018046890 A1 | 3/2018 |
| WO | 2018112458 A1 | 6/2018 |
| WO | 2018200794 A1 | 11/2018 |
| WO | 2020077436 A1 | 4/2020 |
| WO | 2020163780 A1 | 8/2020 |
| WO | 2020167828 A1 | 8/2020 |

OTHER PUBLICATIONS

Balbino et al., "A Comparative Study Between Two Different Conventional Working Electrodes for Detection of Δ9-tetrahydrocannibinol Using Square-Wave Voltammetry: a New Sensitive Method for Forensic Analysis," J. Braz. Chem. Soc., vol. 25, No. 3, 589-596, 2014 (Year: 2014).*
Novak et al., "Voltammetry of Immobilized Particles of Cannabinoids," Electroanalysis 2013, 25, No. 12, 2631-2636 (Year: 2013).*
Royal Society of Chemistry definition of "Differential pulse anodic stripping voltammetry". Downloaded Apr. 21, 2022 from https://www.rsc.org/publishing/journals/prospect/ontology.asp?id=CMO:0000043&MSID=B719207J#:~:text=Definition%3A%20An%20electrochemical%20technique%20where,voltage%20pulses%20of% (Year: 2022).*
"Behest." Merriam-Webster.com Dictionary, Merriam-Webster, https://www.merriam-webster.com/dictionary/behest. Accessed Apr. 21, 2022. (Year: 2022).*
Wanklyn et al., "Disposable Screen Printed Sensor for the Electrochemical Detection of Delta-9-tetrahydrocannabinol in Undiluted Saliva," Chemistry Central Journal, 10(1):1-11 (2016).
Renaud-Young et al., "Development of an ultra-sensitive electrochemical sensor for Δ-tetrahydrocannabinol (THC) and its metabolites using carbon paper electrodes," Electrochimica Acta, 307:351-359 (2019).
Himes et al., "Cannabinoids in Exhaled Breath following Controlled Administration of Smoked Cannabis," Clin Chem., 59(12):1780-1789 (2013).
Beck et al., "Detection of Δ9-Tetrahydrocannabinol in Exhaled Breath Collected from Cannabis Users," Journal of Analytical Toxicology, 35: 541-544 (2011).
International Search Report dated Jul. 15, 2020, in corresponding PCT Application No. PCT/US2020/017746.
Written Opinion dated Jul. 15, 2020, in corresponding PCT Application No. PCT/US2020/017746.
Karimi et al., "Design and Development of Electrochemical Analyzer for Detection of Delta9-Tetrahydrocannabinol," ECS Meeting Abstracts, MA2018-01 2433 (2018).
Abstract of Balbino et al., "Voltammetric determination of D9-THC in glassy carbon electrode: An important contribution to forensic electroanalysis," Forensic Science International, 221(1-3):29-32 (2012).
Abstract of Kokubun et al., "Novel method of determination of D9-tetrahydrocannabinol (THC) in human serum by high-performance liquid chromatography with electrochemical detection," Gan To Kagaku Ryoho, 41:471-473 (2014).
Abstract of Nakahara et al., "Confirmation of cannabis use. II. Determination of tetrahydrocannabinol metabolites in urine and plasma by HPLC with ECD," Journal of Analytical Toxicology, 13:22-24 (1989).
Nissim et al., "Absorptive stripping voltammetry for cannabis detection," Chemistry Central Journal, 9:41 (2015).
Abstract of Beck et al., "Detection of drugs of abuse in exhaled breath using a device for rapid collection: comparison with plasma, urine and self-reporting in 47 drug users," J. Breath Res., 7(2):026006 (2013).
Printout of www.sensabues.com, Sensabues AB, Västerås, Sweden, accessed Oct. 25, 2022.
Balbino et al., "Voltammetric determination of Δ9-THC in glassy carbon electrode: An important contribution to forensic electroanalysis," Forensic Science International 221:29-32 (2012).
Printout of http://sensabues.com/product/nggallery/thumbnails and hyperlinked user instructions at http://sensabues.com/wp-content/uploads/2016/11/Sensabues-user-instructions.pdf, Sensabues AB, Västerås, Sweden (2019), accessed Mar. 7, 2023.

* cited by examiner

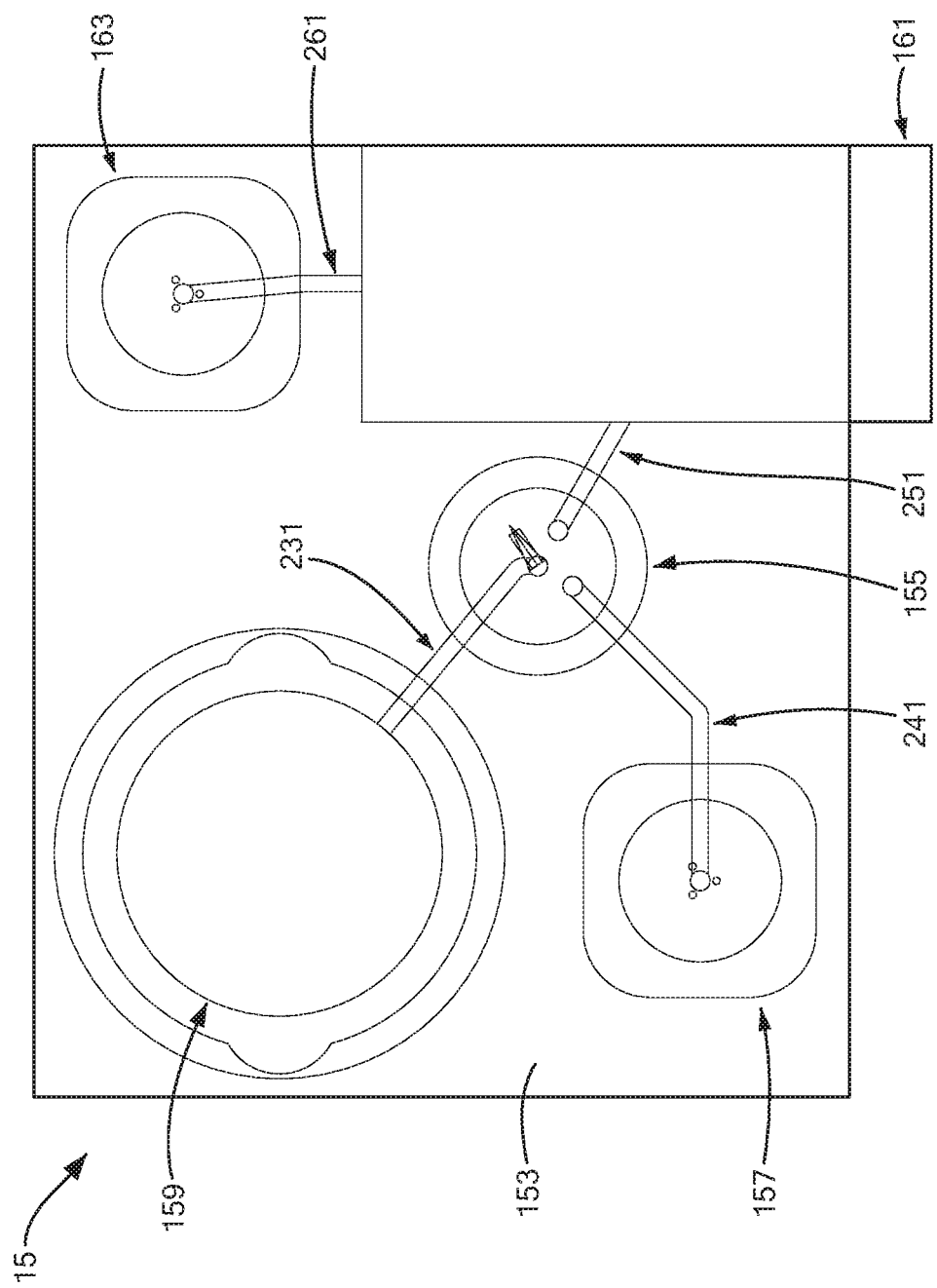

METHOD AND SYSTEM FOR DETECTION AND/OR QUANTIFICATION OF DELTA-9-TETRAHYDROCANNABINOL IN EXHALED BREATH

CROSS-REFERENCE TO RELATED APPLICATIONS

The present application claims the benefit under 35 U.S.C. 119(e) of U.S. Provisional Patent Application No. 62/803,764, inventors Badawi Dweik, filed Feb. 11, 2019, the disclosure of which is incorporated herein by reference.

FEDERALLY SPONSORED RESEARCH OR DEVELOPMENT

This invention was made with government support under 1R43DA041225-01A1 and 2R44DA041225-02 awarded by National Institutes of Health. The government has certain rights in the invention.

BACKGROUND OF THE INVENTION

The present invention relates generally to the detection and/or quantification of $\Delta^9$-tetrahydrocannibinol (THC) in a sample and relates more particularly to a novel method and system for detecting and/or quantifying THC in a sample.

Marijuana use can present both an individual safety hazard and a public safety hazard, particularly when such use results in the operation of a motor vehicle by a driver who is under the influence of marijuana. Driving accidents are prevalent throughout the U.S. In fact, in the U.S., motor vehicle accidents constitute the leading cause of death for individuals ages 8 through 24 and constitute the fifth leading cause of death overall. After alcohol, marijuana is the second most frequently found substance in the bodies of drivers involved in fatal automobile accidents. Driving under the influence of marijuana is reported to double the risk of crash involvement. Additionally, marijuana is the most commonly used illicit drug in the majority of the U.S. The 2014 National Roadside Survey conducted by the National Highway Traffic Safety Administration revealed that approximately 20% of tested drivers have drugs in their system. Furthermore, the number of drivers influenced by marijuana increased by almost 50% during the period from 2007 to 2014, outnumbering those intoxicated by alcohol. For example, in the state of Colorado (where medical marijuana was legalized in 2009 and recreational marijuana was legalized in 2012), marijuana-related traffic deaths have increased over 250% from 2006 to 2015.

$\Delta^9$-tetrahydrocannibinol (THC) is the primary psychoactive substance in marijuana. THC binds to receptors in the brain and impairs cognition and psychomotor function in a dose-related manner. THC levels in blood drop dramatically following cessation of use, yet levels in body fat increase over a period of hours or days, slowly releasing metabolites into the bloodstream. This slow clearance rate from body fat is the main reason why trace cannabinoids can still be detected in blood or urine for many days or weeks following cessation of use. However, while THC and/or its metabolites may be detected in blood or urine long after ingestion, the acute psychoactive effects of marijuana ingestion typically last for mere hours, not days or weeks. More specifically, studies have shown that the adverse effect of marijuana use on driving is limited to the first few hours, with maximal impairment found 20 to 40 minutes after smoking and with most of the impairment gone three hours later.

Existing urine and blood-based THC detection technologies are not adequate for assessing recent exposure to determine if a driver was operating under the influence. A common problem with existing urine tests is that they typically detect non-psychoactive marijuana metabolites for days to weeks after use—long after impairment has passed; consequently, such urine tests do not prove recent use during a suspected period of impairment. A common problem with blood tests is that, although they can detect the presence of active THC at high levels indicating recent use, immediate sample collection is necessary to accurately assess the impairment state. Also, there is strong debate about the correlation between THC levels in blood and the amount of impairment. Additionally, blood sample collection is an invasive method that requires a licensed phlebotomist or a medical professional whereas such an individual is unlikely to be available at the scene of a suspected case of driving under the influence (DUI).

For at least the reasons discussed above, several alternative approaches have been explored for use in identifying drivers suspected of recent marijuana use. Some of these alternative approaches have involved examining samples of saliva, and others of these alternative approaches have involved examining samples of exhaled breath. One issue that makes approaches involving samples of saliva more complicated than approaches involving samples of exhaled breath is that samples of saliva also typically contain significant quantities of DNA, which can be used to identify an individual. Therefore, for example, in the US, the collection of saliva samples by law enforcement or other government officials may implicate protected constitutional rights.

An example of an approach that uses exhaled breath to detect substances like THC is disclosed in PCT International Publication No. WO 2012/120140, which was published Sep. 13, 2012, and which is incorporated herein by reference. More specifically, according to the aforementioned publication, there is disclosed a portable drug sampling device for handheldly collecting a sample from exhaled breath of a subject for analysis by a method like spectroscopy or preferably mass spectroscopy or Surface enhanced Raman spectroscopy. The device comprises a housing comprising at least one inlet and at least one outlet for the exhaled breath to exit through. A sampling membrane is arranged in the housing. A tubular element having a mouthpiece section for the subject to exhale into is provided, and a saliva trap section comprising baffles to create a non-straight gas flow path for letting aerosols pass through the tubular element is also provided. The sampling membrane is arranged to collect the aerosols from the exhaled breath. The portable drug testing device further comprises a volume collecting element.

Another example of an approach that uses exhaled breath to detect substances like THC is disclosed in U.S. Patent Application Publication No. US 2015/0305651 A1, inventors Attariwala et al., which was published Oct. 29, 2015, and which is incorporated herein by reference. According to the aforementioned publication, there is disclosed a system for collecting cannabis and the psychoactive component tetrahydrocannabinol from a sample of exhaled breath. Single or multiple exhaled breaths are conditioned by removing contaminants, and regulating flow rate and/or pressure to collect a sample of tetrahydrocannabinol for timely local or remote analysis. The cannabis detection system comprises a containment trap for removing interfering materials from the breath of the subject and a collection component for sampling components of breath introduced into the system through the containment trap for analysis to determine a presence of THC in the breath. Analysis techniques may involve high performance liquid chromatography and/or mass spectrometry.

One disadvantage that the present inventors have identified with approaches of the above-discussed types involving breath samples is that such approaches typically require analysis techniques and instrumentation that do not readily lend themselves to use outside of a laboratory setting by individuals lacking laboratory training. As a result, such approaches have limited value in applications like roadside testing of suspected drugged drivers by law enforcement officers.

Other documents that may be of interest may include the following, all of which are incorporated herein by reference: U.S. Pat. No. 9,429,564 B2, inventor Beck, issued Aug. 30, 2016; U.S. Pat. No. 9,011,657 B2, inventors Parselle et al., which issued Apr. 21, 2015; U.S. Pat. No. 8,877,038 B2, inventors Kampouris et al., issued Nov. 4, 2014; U.S. Pat. No. 7,790,400 B2, inventors Jehanli et al., issued Sep. 7, 2010; U.S. Patent Application No. US 2015/0033824, inventors Hammarlund et al., published Feb. 5, 2015; U.S. Patent Application Publication No. US 2009/0294298 A1, inventors Compton et al., published Dec. 3, 2009; PCT International Publication No. WO 2018/112458 A1, which was published Jun. 21, 2018; PCT International Publication No. WO 2009/081153 A2, published Jul. 2, 2009; Renaud-Young et al., "Development of an ultra-sensitive electrochemical sensor for $\Delta^9$-tetrahydrocannabinol (THC) and its metabolites using carbon paper electrodes," *Electrochimica Acta*, 307:351-359 (2019); Himes et al., "Cannabinoids in Exhaled Breath following Controlled Administration of Smoked Cannabis," *Clin Chem.*, 59(12):1780-1789 (2013); and Beck et al., "Detection of $\Delta^9$-Tetrahydrocannabinol in Exhaled Breath Collected from Cannabis Users," *Journal of Analytical Toxicology*, 35: 541-544 (2011).

SUMMARY OF THE INVENTION

It is an object of the present invention to provide a new technique for detecting and/or quantifying $\Delta^9$-tetrahydrocannibinol (THC) in exhaled breath.

It is another object of the present invention to provide a technique as described above that overcomes at least some of the disadvantages associated with existing techniques for detecting and/or quantifying $\Delta^9$-tetrahydrocannibinol (THC) in exhaled breath.

Therefore, according to one aspect of the invention, there is provided a method for detecting and/or quantifying $\Delta^9$-tetrahydrocannibinol (THC) in exhaled breath, the method comprising the steps of (a) providing an electrochemical sensing element; (b) providing a filter that traps THC in exhaled breath; (c) causing a subject to exhale onto the filter, whereby at least some of the THC, if present in an exhaled breath, is trapped in the filter; (d) washing the filter with an eluent, whereby at least some of the THC trapped in the filter is eluted therefrom in an eluate; (e) depositing the eluate from the filter onto the electrochemical sensing element; (f) drying the eluate on the electrochemical sensing element, whereby at least some of the THC in the eluate is immobilized on the electrochemical sensing element; and (g) directly electrochemically detecting and/or quantifying the immobilized THC.

In a more detailed feature of the invention, the electrochemical sensing element may comprise a working electrode, a counter electrode, and a reference electrode.

In a more detailed feature of the invention, the working electrode, the counter electrode, and the reference electrode may be screen-printed electrodes on a substrate.

In a more detailed feature of the invention, the screen-printed electrodes may be devoid of surface treatment.

In a more detailed feature of the invention, the drying step may comprise using a vacuum.

In a more detailed feature of the invention, the drying step may comprise using a heater.

In a more detailed feature of the invention, the drying step may comprise using an air blower.

In a more detailed feature of the invention, the drying step may comprise air-drying the deposited eluate.

In a more detailed feature of the invention, the detecting and/or quantifying step may comprise performing a pulse voltammetry technique to obtain a measurement and comparing said measurement to a standard.

In a more detailed feature of the invention, the pulse voltammetry technique may be performed in the presence of an aqueous alkaline electrolyte.

In a more detailed feature of the invention, the pulse voltammetry technique may comprise square-wave voltammetry.

In a more detailed feature of the invention, the pulse voltammetry technique may comprise differential pulse anodic voltammetry.

In a more detailed feature of the invention, at least one of steps (c), (d), (e), (f), and (g) may be automated.

In a more detailed feature of the invention, the method may further comprise the step of displaying a result of step (g).

In a more detailed feature of the invention, the eluent may comprise at least one alcohol.

In a more detailed feature of the invention, the at least one alcohol may comprise at least one member selected from the group consisting of methanol, ethanol, 1-propanol, and isopropanol.

In a more detailed feature of the invention, the liquid may further comprise water.

In a more detailed feature of the invention, the liquid may further comprise a surfactant.

In a more detailed feature of the invention, the causing step may comprise having a first individual blow onto the filter at the behest of a second individual.

According to another aspect of the invention, there is provided a system for use in detecting and/or quantifying $\Delta^9$-tetrahydrocannibinol (THC) in exhaled breath, the system comprising (a) a collection device, the collection device comprising a filter that traps THC in exhaled breath; (b) an analysis cartridge, the analysis cartridge comprising (i) a support, the support comprising a receptacle for receiving the filter from the collection device, (ii) an electrochemical sensing element coupled to the support, the electrochemical sensing element comprising a working electrode, (iii) a quantity of an eluent solution coupled to the support for use in eluting THC from the filter in an eluate deposited onto the working electrode, (iv) a quantity of an electrolytic solution coupled to the support for use in performing an electrochemical analysis, and (c) a reader, the reader adapted to be electrically coupled to the electrochemical sensing element and comprising a potentiostat and a controller for directly determining the presence and/or quantity of THC on the working electrode.

In a more detailed feature of the invention, the collection device may further comprise a filter holder, and the filter may be removably mounted in the filter holder.

In a more detailed feature of the invention, the collection device may further comprise a filter cap, and the filter cap may be removably mounted on the filter holder, with the filter being positioned sandwiched between the filter holder and the filter cap.

In a more detailed feature of the invention, the collection device may further comprise a body, the body may have a fluid channel, and the filter holder may be removably mounted in the body, with the filter in fluid communication with the fluid channel of the body.

In a more detailed feature of the invention, the reader may further comprise a container, and the container may comprise a drawer onto which the analysis cartridge may be removably seated.

In a more detailed feature of the invention, the reader may further comprise a dryer for drying the eluate.

In a more detailed feature of the invention, the dryer may comprise at least one of a heater, a vacuum, and an air blower.

In a more detailed feature of the invention, the reader may further comprise a display for displaying a result of the determination of the presence and/or quantity of THC on the working electrode.

According to still another aspect of the invention, there is provided an analysis cartridge for use in determining the presence or quantity of $\Delta^9$-tetrahydrocannibinol (THC) in a fluid sample, the analysis cartridge comprising (a) a support, the support comprising a receptacle for receiving a filter; (b) a press movably mounted in the receptacle for use in applying pressure to the filter; (c) an electrochemical sensing element coupled to the support, the electrochemical sensing element comprising a working electrode; (d) a first fluid pack, the first fluid pack being coupled to the support and comprising a quantity of an eluent solution; (e) a second fluid pack, the second fluid pack being coupled to the support and comprising a quantity of an electrolytic solution; (f) a valve, the valve coupled to the support; (g) a first fluid conduit in the support for use in fluidly coupling the receptacle to the valve; (h) a second fluid conduit in the support for use in fluidly coupling the first fluid pack to the valve; (i) a third fluid conduit in the support for use in fluidly coupling the valve to a first space directly above the electrochemical sensing element; and (j) a fourth fluid conduit in the support for use in fluidly coupling the second fluid pack to a second space directly above the electrochemical sensing element.

Additional objects, as well as aspects, features and advantages, of the present invention will be set forth in part in the description which follows, and in part will be obvious from the description or may be learned by practice of the invention. In the description, reference is made to the accompanying drawings which form a part thereof and in which is shown by way of illustration various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. These drawings are not necessarily drawn to scale, and certain components may have undersized and/or oversized dimensions for purposes of explication. In the drawings wherein like reference numeral represent like parts:

FIG. 8(a) through 8(c) are enlarged top perspective, enlarged top, and enlarged bottom views, respectively, of the analysis cartridge shown in FIG. 1;

DETAILED DESCRIPTION OF THE INVENTION

The present invention is directed at a testing device and method to enable detection and/or quantification of THC levels in breath samples. In a preferred embodiment, the present invention permits real-time detection and/or quantification at a point-of-collection for roadside use. This portable, cost-effective and non-invasive electrochemical sensor device for near real-time THC detection will fill urgent, unmet needs as an effective alternative to current expensive and time-consuming analytical techniques which have a turnaround time of several days. A key accomplishment is the development of a method that extracts THC from breath aerosol and immobilizes and pre-concentrates the THC on a disposable screen-printed sensor chip, thereby allowing direct electrochemical measurement with a short response time and high sensitivity.

Figure 1:
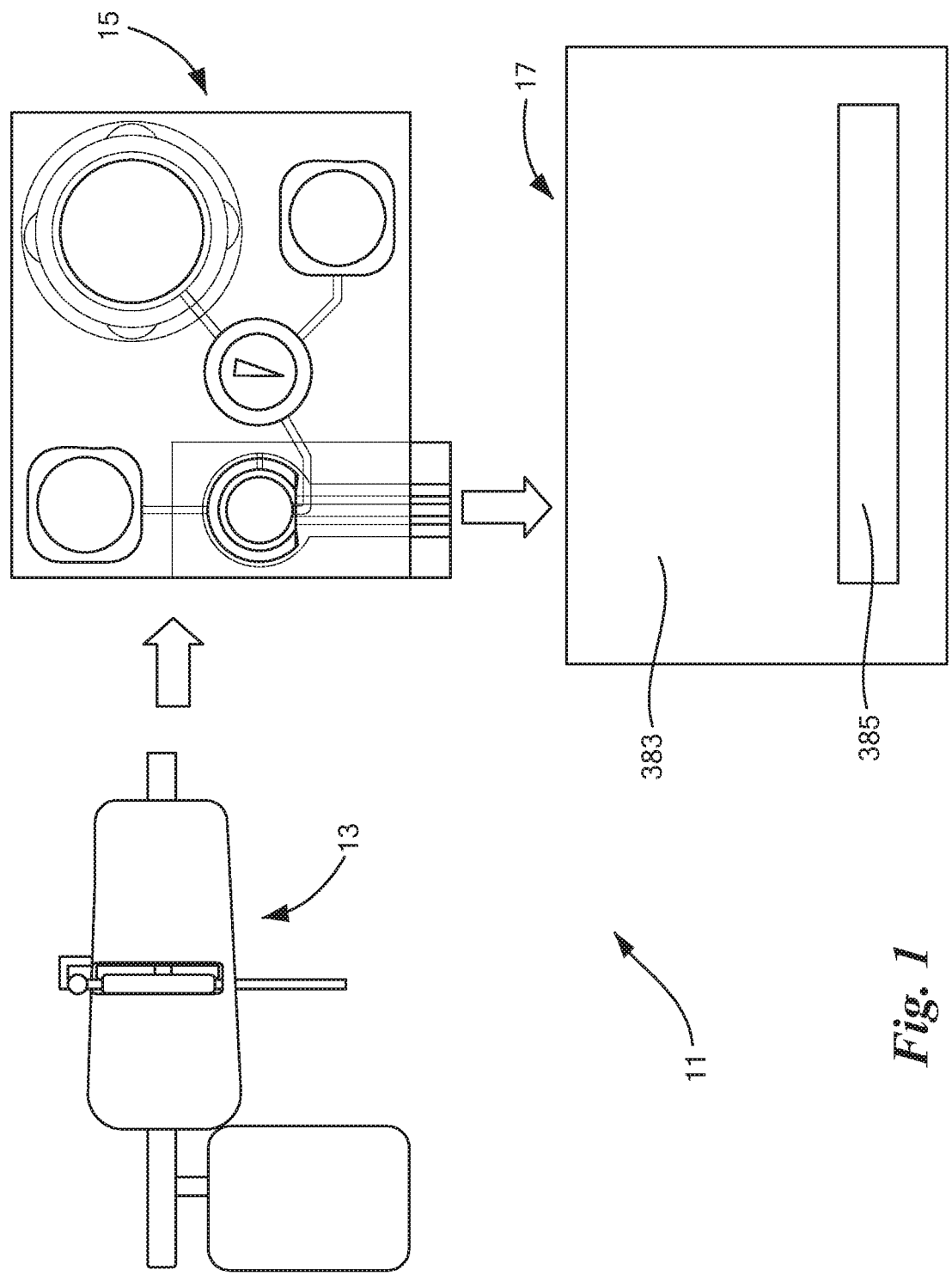
FIG. 1 is a simplified view of one embodiment of a system constructed according to the present invention for detecting and/or quantifying $\Delta^9$-tetrahydrocannibinol (THC) in exhaled breath, the system being shown prior to use.

Referring now to FIG. 1, there is shown a simplified view of one embodiment of a system for detecting and/or quantifying Δ⁹-tetrahydrocannibinol (THC) in exhaled breath, the system being constructed according to the present invention and being represented generally by reference numeral 11. Details of system 11 that are not critical to an understanding of the present invention may be omitted from the drawings of the present application or from the accompanying description herein or may be described herein in a simplified manner.

System 11 may comprise a collection device 13, an analysis cartridge 15, and a reader 17.

Figure 2A:
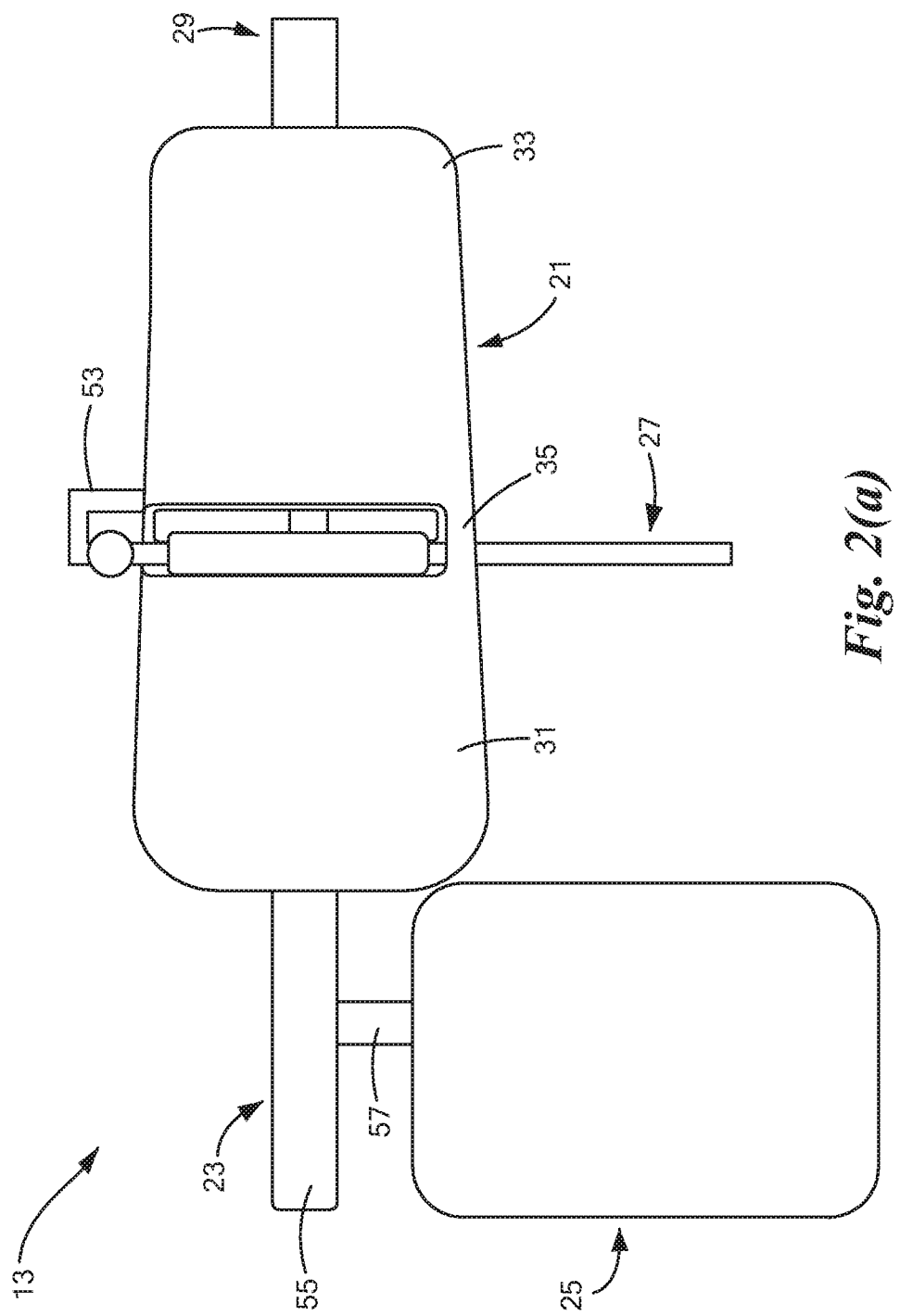
FIG. 2(a) is a side view, broken away in part, of the collection device shown in FIG. 1.
Figure 2B:
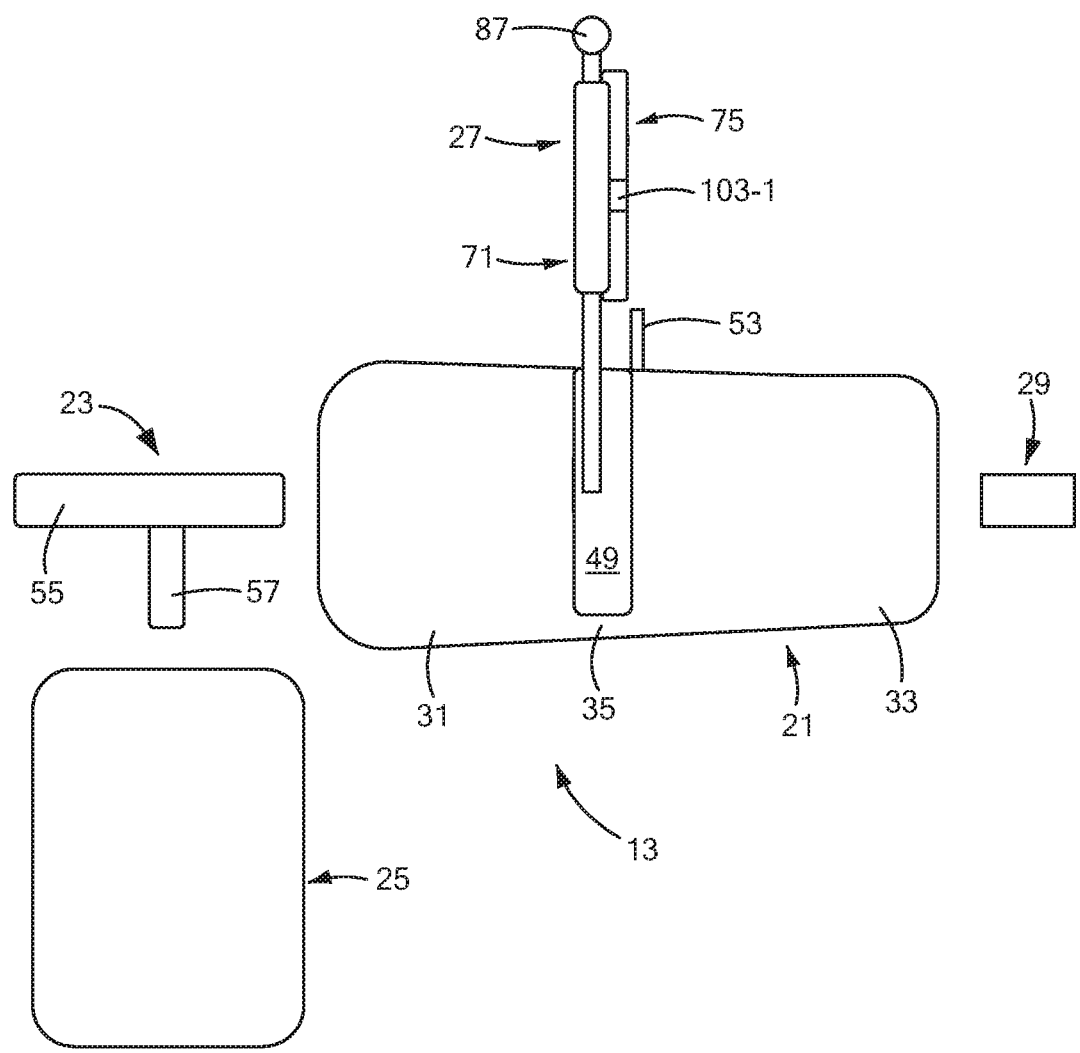
FIG. 2(b) is a partly exploded side view of the collection device shown in FIG. 2(a)

Referring now to FIGS. 2(a) and 2(b), there is shown one embodiment of collection device 13. As can be seen, collection device 13 may comprise a body 21, a mouthpiece 23, an inflatable receptacle 25, a filter assembly 27, and an outlet tube 29.

Figure 3A:
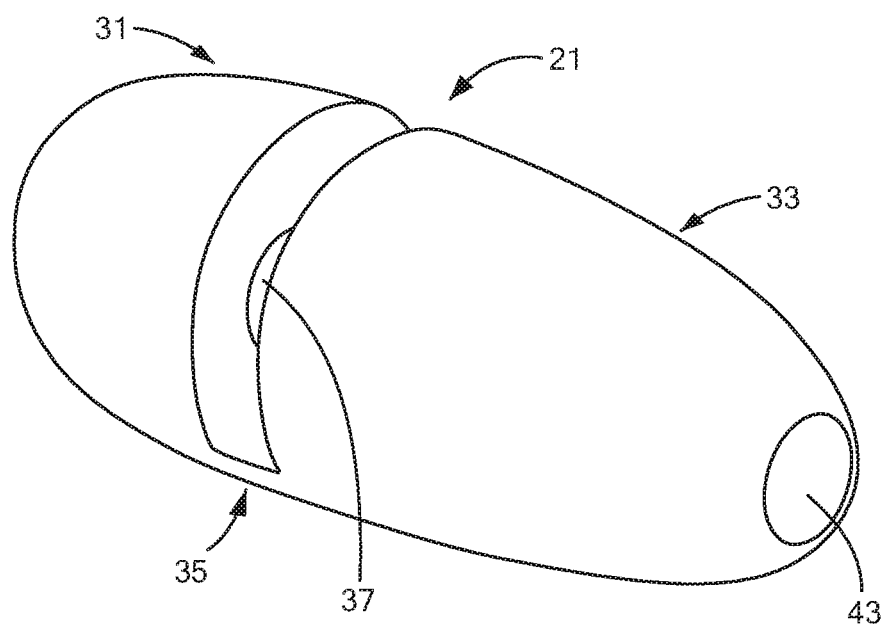
FIGS. 3(a) and 3(b) are enlarged perspective and enlarged longitudinal section views, respectively, of the collection device body shown in FIG. 2(a)
Figure 3B:
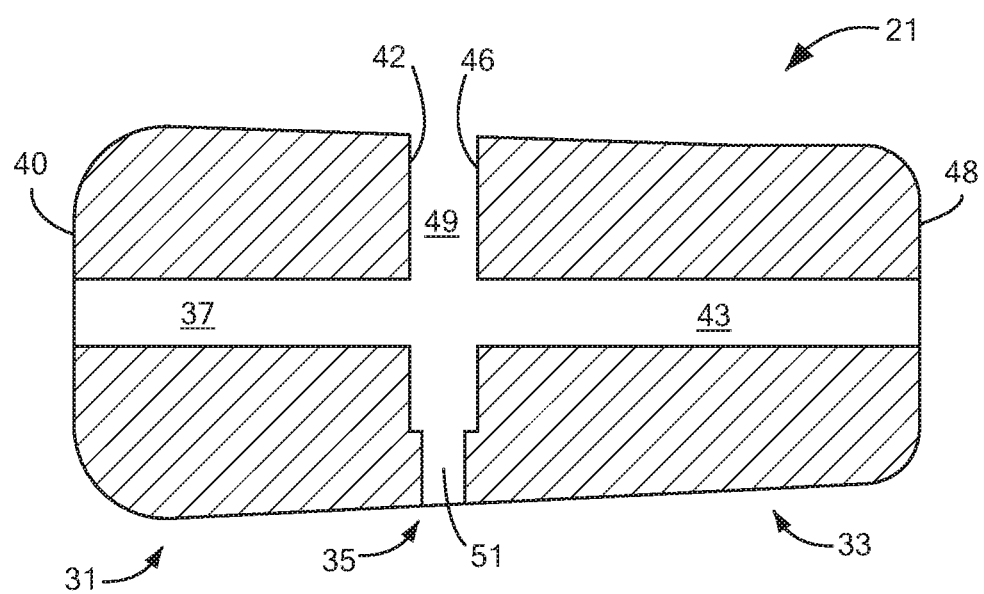

Body 21, which is also shown separately in FIGS. 3(a) and 3(b), may be a unitary (i.e., one-piece) structure made of a rigid material, such as a suitable molded plastic or the like. Body 21 may be a generally tubular structure shaped to include a proximal portion 31, a distal portion 33, and an intermediate portion 35.

Proximal portion 31 may be shaped to comprise a fluid channel 37, which may extend generally along the longitudinal centerline of proximal portion 31 and which may terminate at a proximal end 40 of proximal portion 31 and at a distal end 42 of proximal portion 31. Distal portion 33 may be shaped to comprise a fluid channel 43, which may extend generally along the longitudinal centerline of distal portion 33 and which may terminate at a proximal end 46 of distal portion 33 and at a distal end 48 of distal portion 33. Fluid channel 37 of proximal portion 31 and fluid channel 43 of distal portion 33 may be generally aligned with one another. Intermediate portion 35 of body 21 may extend between and may interconnect the respective bottoms of distal end 42 of proximal portion 31 and proximal end 46 of distal portion 33. Proximal portion 31, distal portion 33, and intermediate portion 35 may collectively form a cavity 49, which may be sized and shaped to matingly receive a disc-shaped portion of filter assembly 27. A transverse opening 51 may be provided in intermediate portion 35 to receive an elongated distal portion of filter assembly 27. A latch 53 may be rotatably mounted on proximal end 46 of distal portion 33 and may be used to selectively engage a portion of filter assembly 27 so as to selectively secure filter assembly 27 to body 21.

Figure 4:
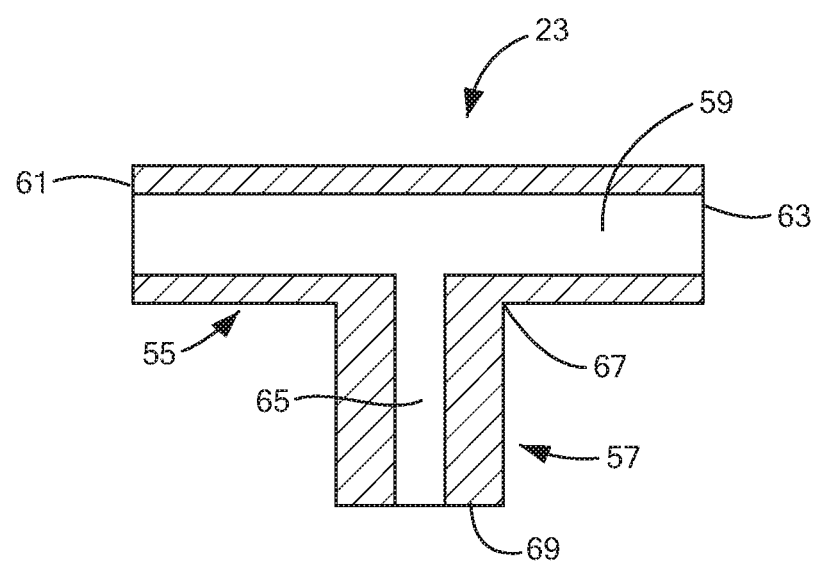
FIG. 4 is an enlarged longitudinal section view of the mouthpiece shown in FIG. 2(a)

Mouthpiece 23, which is also shown separately in FIG. 4, may be a unitary (i.e., one-piece) structure made of a rigid material, such as a suitable molded plastic or the like. Mouthpiece 23, which may be "T-shaped," may comprise a first tubular portion 55 and a second tubular portion 57. First tubular portion 55 may be shaped to include a fluid channel 59 extending from a proximal end 61 of first tubular portion 55 to a distal end 63 of first tubular portion 55, and second tubular portion 57 may be shaped to include a fluid channel 65 extending from a proximal end 67 of second tubular portion 57 to a distal end 69 of second tubular portion 57. First tubular portion 55 and second tubular portion 57 may be arranged so that fluid channel 59 and fluid channel 65 are in fluid communication with one another.

First tubular portion 55 of mouthpiece 23 may be fixedly mounted within fluid channel 37 of body 21 so that (i) distal end 63 of first tubular portion 55 is disposed within fluid channel 37 (thereby placing fluid channel 59 and fluid channel 37 in fluid communication with one another), (ii) proximal end 61 of first tubular portion 55 is spaced proximally from proximal portion 31, and (iii) second tubular portion 57 is positioned proximal relative to proximal portion 31.

Although, in the present embodiment, first tubular portion 55 is shown as a straight tube, with proximal end 61 and distal end 63 being aligned with one another, it is to be understood that one could modify first tubular portion 55 so that it is bent, with distal end 63 being elevated relative to proximal end 61. For example, this may be done by providing first tubular portion 55 with a "stepped" shape. Such an arrangement may be desirable in minimizing the extent to which mucus and other undesired fluids and solids may pass through distal end 63 of first tubular portion 55. In such a stepped arrangement, second tubular portion 57 may be joined to first tubular portion 55 along the elevated portion of first tubular portion 55.

First tubular portion 55 and second tubular portion 57 may be configured relative to one another so that, for each exhaled breath blown into the proximal end of fluid channel 59, a first portion or fraction passes through the distal end of fluid channel 59 and a second portion or fraction passes through the distal end of fluid channel 65.

Inflatable receptacle 25 may be fixedly or removably coupled to second tubular portion 57 of mouthpiece 23 so that inflatable receptacle 25 and second tubular portion 57 are in fluid communication with one another. Inflatable receptacle 25 may comprise a non-elastic bag, preferably made of plastic, or an elastic balloon. A non-elastic bag may be preferred over an elastic balloon since a non-elastic bag typically requires less force to be inflated and will automatically stop when fully inflated. As can be appreciated, inflatable receptacle 25 may be used to provide a visual indication that a sufficient sample of exhaled breath has been sampled. In fact, by knowing the fluid volumetric capacity of inflatable receptacle 25 and the relative fractions of an exhaled breath that pass through first tubular portion 55 and second tubular portion 57, one can determine the entire gas volume that has been sampled.

Although not shown in the present embodiment, inflatable receptacle 25 may be equipped with a one-way valve that ensures that an exhaled breath can enter inflatable receptacle 25 but cannot leave.

Figure 5:
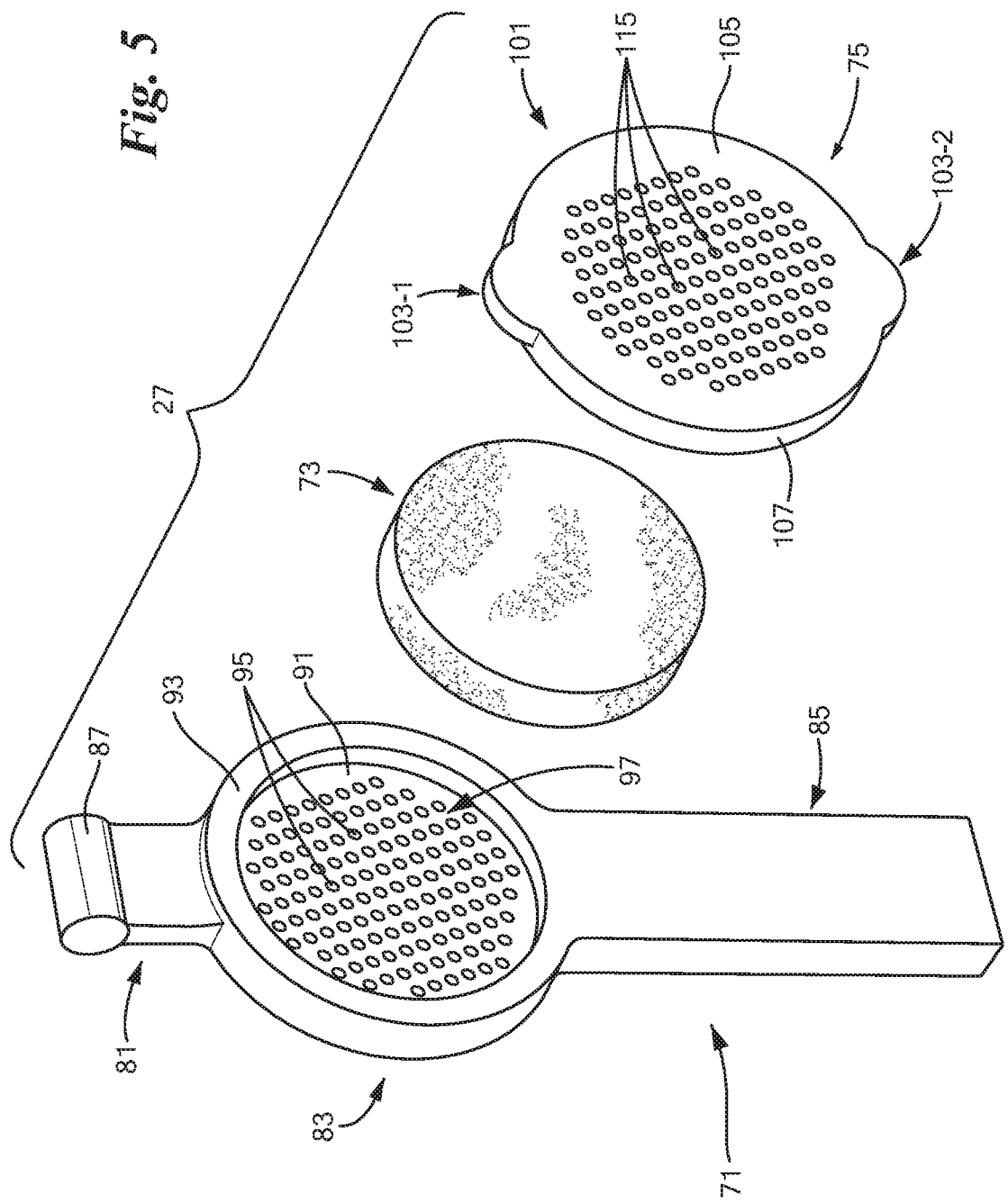
FIG. 5 is an exploded perspective view of the filter assembly shown in FIG. 2(a)

Filter assembly 27, which is also shown separately in FIG. 5, may comprise a holder 71, a filter 73, and a filter cap 75. Holder 71, which may be a unitary (i.e., one-piece) structure made of a rigid material, such as a suitable molded plastic or the like, may be shaped to comprise a proximal portion 81, an intermediate portion 83, and a distal portion 85. Proximal portion 81, which may be used to permit grasping of filter assembly 27 so as to facilitate insertion of filter assembly 27 into body 21 and/or removal of filter assembly 27 from body 21, may be shaped to include an elongated planar structure having a rounded proximal end 87. Intermediate portion 83, which may be used to receive filter 73, may comprise a supporting wall 91 and a side wall 93. Supporting wall 91, which may be used to support one of the two opposing major surfaces of filter 73, may be a disc-shaped structure. A plurality of transverse openings 95 may be provided in supporting wall 91, openings 95 being designed to permit fluid to pass freely through supporting wall 91. Side wall 93 may extend distally from around the periphery of supporting wall 91, with supporting wall 91 and side wall 93 collectively defining a cavity 97 dimensioned to receive filter 73. Distal portion 85 of holder 71 may be an elongated planar structure dimensioned to be removably inserted through transverse opening 51 in intermediate portion 35 of body 21. In this manner, distal portion 85 may help to secure holder 71 in body 21.

Filter 73 may be an electrostatic filter membrane of the type described in U.S. Pat. No. 9,429,564 B2 and U.S. Patent Application Publication No. US 2015/0033824 A1, which electrostatic filter membrane may be used to selectively filter certain non-volatile substances like THC in aerosol from exhaled breath.

During breathing, micro-particles in aerosol are formed. It is estimated that exhaled human breath constitutes about 3000 components, the bulk of which are volatile organic compounds in trace quantities. Many of these vapor-phase compounds will pass through filter 73. The aerosol phase can be collected as exhaled breath condensate and is known to contain proteins and non-volatile metabolites. With its extremely low vapor pressure and low water solubility, THC is expected to exist almost entirely in the solid-phase at room temperature and as a micro-particle aerosol in exhaled breath. The majority of the potentially interfering species in exhaled breath will be excluded because only micro-particle aerosols will be collected by filter 73 (i.e., volatile compounds carried in the vapor phase will be excluded).

In one embodiment, filter 73 may comprise a first layer of non-woven filtration media with a specific weight in the range of 23 $g/m^3$ to 500 $g/m^3$, preferably 150 $g/m^3$ to 300 $g/m^3$, more preferably 200 $g/m^3$ to 280 $g/m^3$. The aforementioned first layer may comprise a blend of acrylic fibers and polypropylene fibers. The acrylic fibers may have electrostatic properties (e.g., corona discharge) while the polypropylene fibers may provide mechanical support. Filter 73 may additionally comprise one or more additional layers that may be used to enhance the physical properties of the filter membrane and/or to enhance the filtration performance of the filter membrane. For example, an additional layer may be a carrier, such as a polypropylene spunbonded carrier. The carrier may have a scrim weight of 10 $g/m^3$ to 20 $g/m^3$. Filter 73 may have a filtration efficiency of 99% for particle sizes of 0.50 to 20 um.

Another material that may be suitable for use as filter 73 may include CDS EMPORE™ solid phase extraction disks, which are commercially available from CDS Analytical LLC (Oxford, Pa.). The aforementioned extraction disks contain an octadecyl (C18) functional group to provide non-polar interactions for analyte capture. Still another material that may be suitable for use as filter 73 may include a non-woven mat of porous polyethylene/polypropylene fibers commercially available as HRM (high release media) from Porex Corporation (Fairburn, Ga.).

Figure 6:
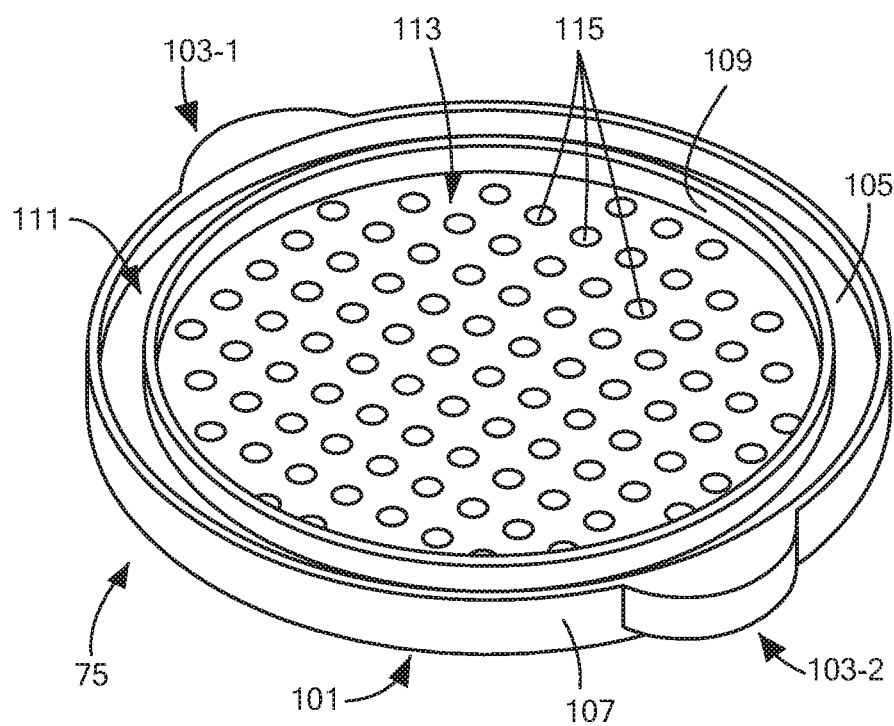
FIG. 6 is an enlarged perspective view of the filter cap shown in FIG. 5.
Figure 7:
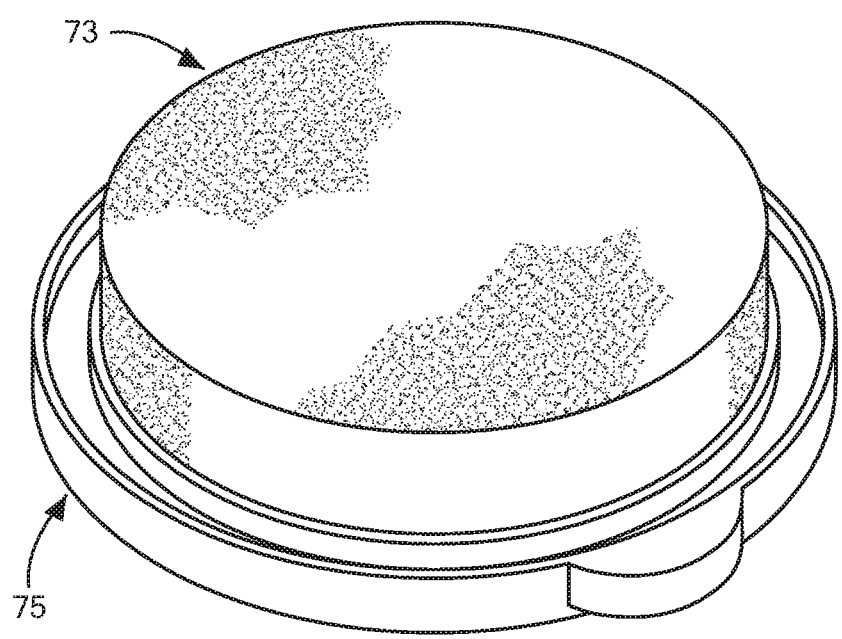
FIG. 7 is a perspective view showing the filter cap of FIG. 6 with a filter mounted thereon.

Filter cap 75, which is also shown separately in FIG. 6, may be a unitary (i.e., one-piece) structure made of a molded plastic or similar material. Filter cap 75 may be shaped to comprise a central portion 101 and a pair of side portions 103-1 and 103-2. Central portion 101, in turn, may be disc-shaped and may comprise a supporting wall 105, an outer side wall 107 extending generally perpendicularly from the periphery of supporting wall 105, and an inner side wall 109 arranged concentrically within outer side wall 107 and extending generally perpendicularly from supporting wall 105. Filter cap 75 may be constructed to have sufficient resiliency so that central portion 101 of filter cap 75 may be removably snap fit onto and removed from intermediate portion 83 of holder 71, with side wall 93 of holder 71 being matingly received in a cavity 111 formed by outer side wall 107, inner side wall 109, and supporting wall 105 of filter cap 75, and with filter 73 being matingly received in a cavity 113 formed by inner side wall 109 and supporting wall 105 of filter cap 75. In this manner, filter 73 may be securely retained between holder 71 and filter cap 75 during sampling; then, after sampling is complete, filter assembly 27 may be removed from body 21, and filter cap 75 and filter 73 may be removed from holder 71, with filter 73 being retained in filter cap 75 (as shown in FIG. 7). A plurality of transverse openings 115 may be provided in the portion of supporting wall 105 located within inner side wall 109, openings 115 being designed to permit fluid to pass freely therethrough.

Side portions 103-1 and 103-2, which may extend radially outwardly from central portion 101 from opposing sides thereof, may be of use in removing filter cap 75 from holder 71 and/or in retaining filter 73 on analysis cartridge 15, as will be discussed further below.

As noted above, filter assembly 27 may be removably mounted in cavity 49 of body 21 to permit filter 73 to be inserted into body 21 for sampling and, thereafter, to be removed therefrom for transfer to analysis cartridge 15. While mounted within cavity 49 of body 21, filter 73 is preferably positioned between and aligned with fluid channel 37 of proximal portion 31 and fluid channel 43 of distal portion 33.

Outlet tube 29, which may be a unitary (i.e., one-piece) structure made of a rigid molded plastic or similar material, may be a tubular member having a proximal end 123, a distal end 125, and a fluid channel 127 extending longitudinally therebetween. Proximal end 123 of outlet tube 29 may be fixedly mounted within fluid channel 43 of distal portion 33 in such a way that fluid channel 127 of outlet tube 29 is in fluid communication with fluid channel 43 of distal portion 33 and so that distal end 48 of outlet tube 29 extends distally beyond distal end 48 of distal portion 33.

Figure 8A:
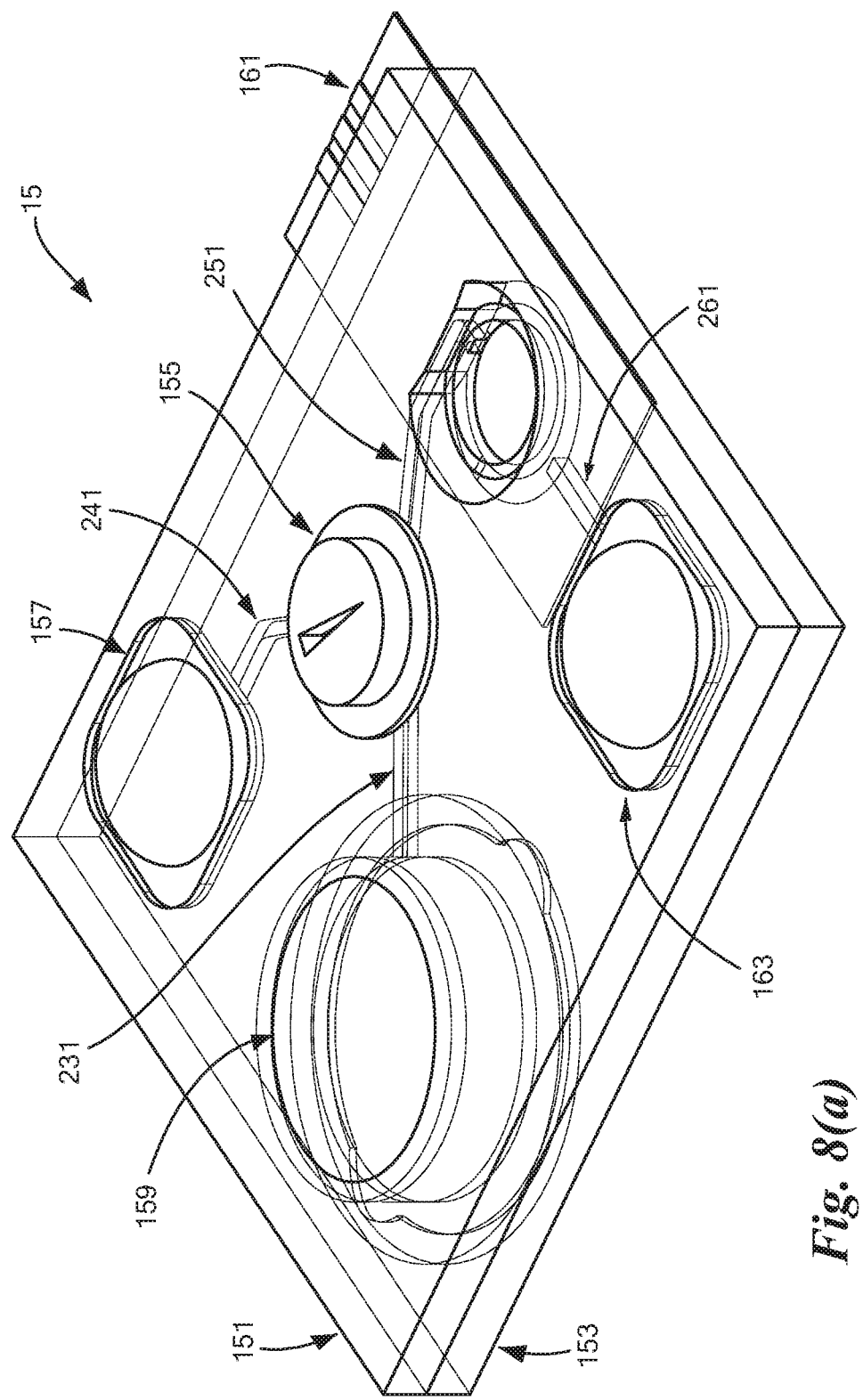
Figure 8B:
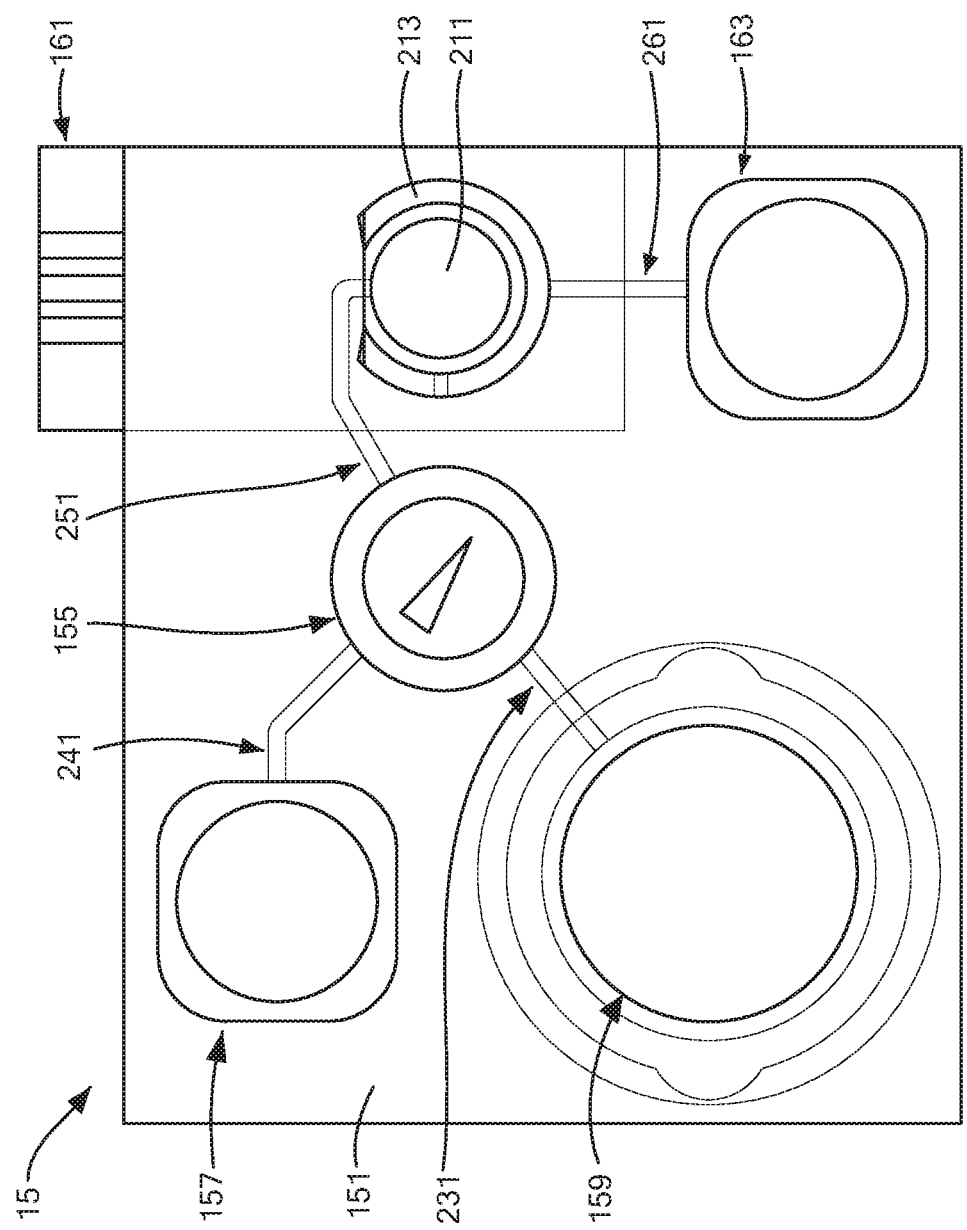

Analysis cartridge 15, which is also shown separately in FIGS. 8(a) through 8(c), may comprise an upper body 151, a lower body 153, a valve 155, a first fluid pack 157, a press 159, a sensor assembly 161, and a second fluid pack 163.

Figure 9A:
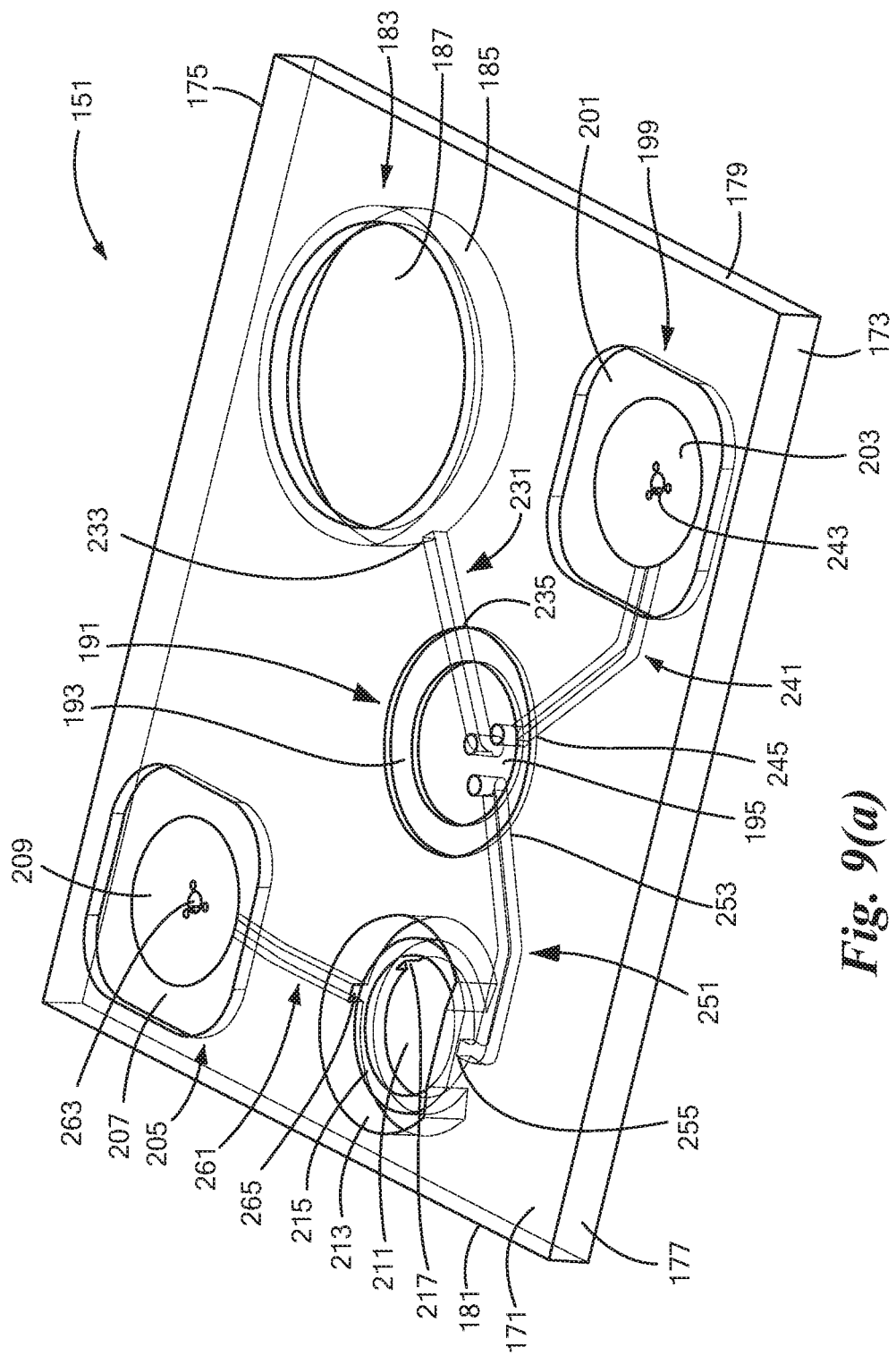
FIGS. 9(a) through 9(c) are top perspective, bottom perspective, and bottom views, respectively, of the upper layer of the analysis cartridge shown in FIG. 8(a)
Figure 9B:
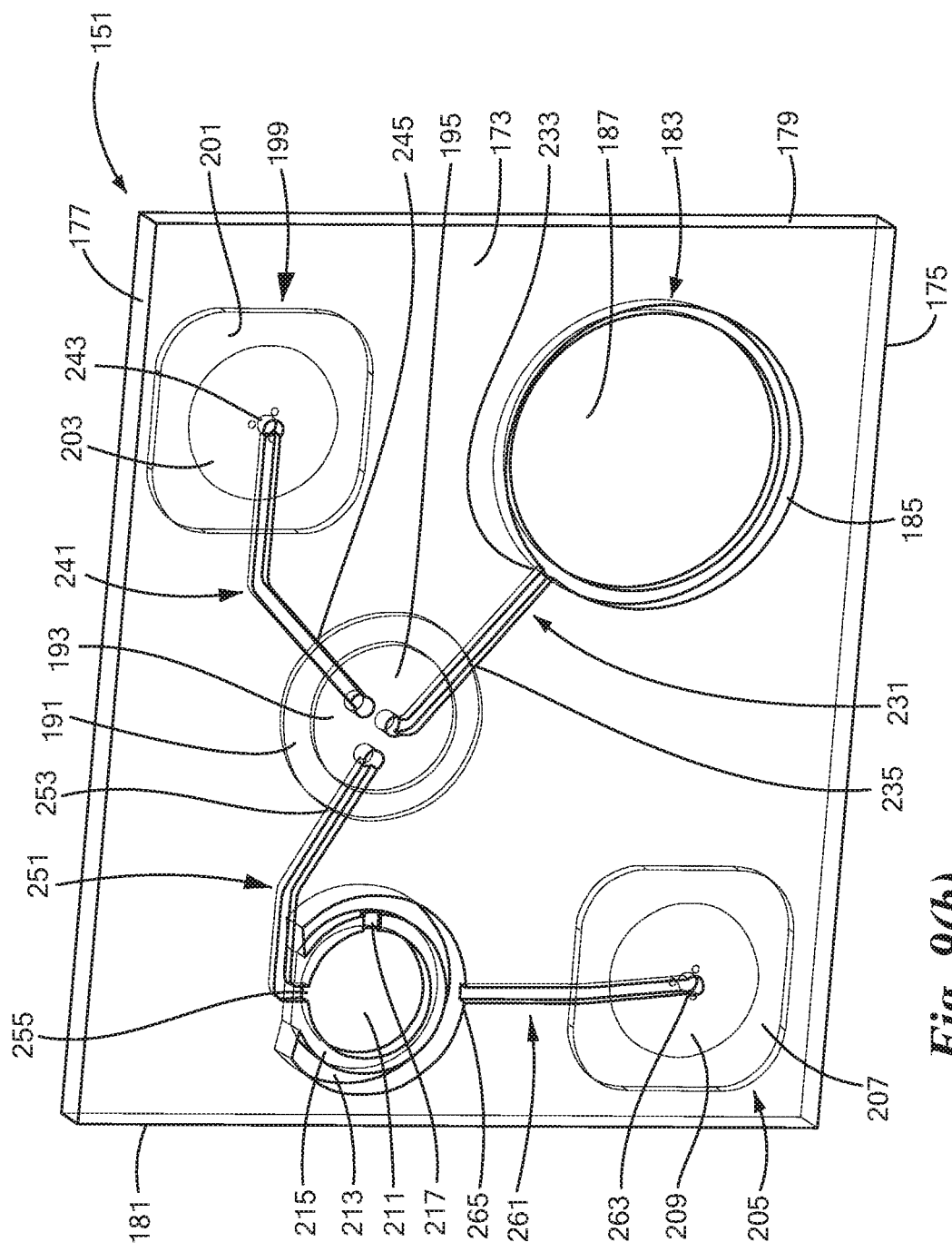
Figure 9C:
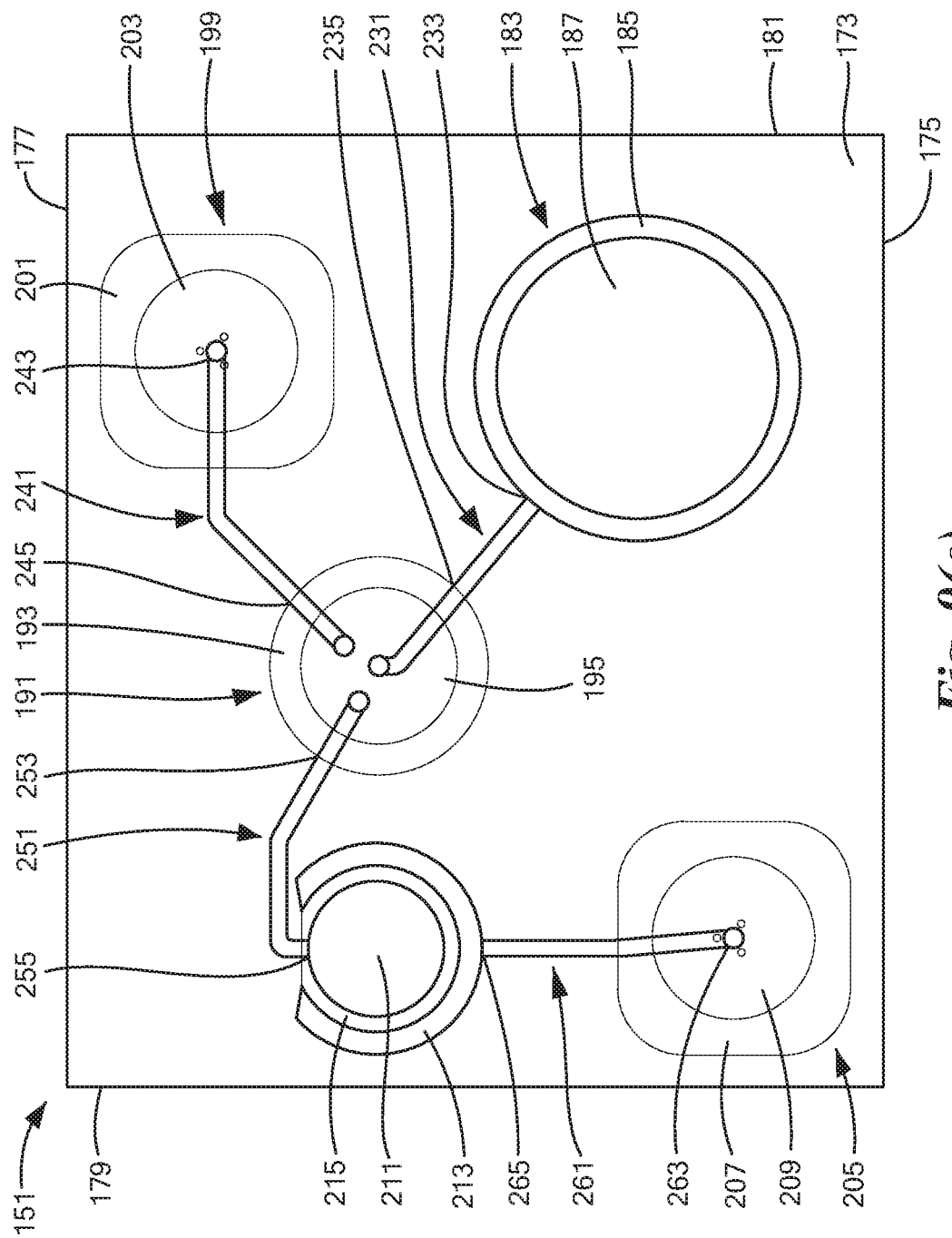

Upper body 151, which is also shown separately in FIGS. 9(a) through 9(c), may be a unitary (i.e., one-piece), generally rectangular, solid, planar structure made of a rigid, electrically non-conductive, chemically inert material, such as a suitable plastic or ceramic. In the present embodiment, upper body 151 is shown as being transparent or translucent, but it need not be. Upper body 151 may be shaped to include a top surface 171, a bottom surface 173, a front surface 175, a rear surface 177, a left side surface 179, and a right side surface 181. In addition, upper body 151 may be shaped to include a number of counterbores, transverse openings and grooves. More specifically, a first counterbore 183, which may be used to receive press 159, may be provided in upper body 151. First counterbore 183 may extend from top surface 171 to bottom surface 173 and may include a lower portion 185 of generally circular cross-section and comparatively greater diameter and an upper portion 187 of generally circular cross-section and comparatively lesser diameter. A second counterbore 191, which may be used to receive valve 155, may be provided in upper body 151. Second counterbore 191 may extend from top surface 171 to bottom surface 173 and may include an upper portion 193 of generally circular cross-section and comparatively greater diameter and a lower portion 195 of generally circular cross-section and comparatively lesser diameter. A third counterbore 199, which may be used to receive first fluid pack 157, may be provided in upper body 151. Third counterbore 199 may extend from top surface 171 to bottom surface 173 and may include an upper portion 201 that is generally square in cross-section and of comparatively greater cross-section and a lower portion 203 that is generally circular in cross-section and of comparatively lesser cross-section. A fourth counterbore 205, which may be used to receive second fluid pack 163, may be provided in upper body 151. Fourth counterbore 205 may extend from top surface 171 to bottom surface 173 and may include an upper portion 207 that is generally square in cross-section and of comparatively greater cross-section and a lower portion 209 that is generally circular in cross-section and of comparatively lesser cross-section.

A first transverse opening 211, which may be aligned with the working electrode of sensor assembly 161, may be provided in upper body 151. First transverse opening 211 may extend from top surface 171 to bottom surface 173 and may have a generally circular cross-section. A second transverse opening 213, which may be aligned with the counter electrode and the reference electrode of sensor assembly 161, may be provided in upper body 151. Second transverse opening 213, which may have a generally truncated circular cross-section, may extend from top surface 171 to bottom surface 173 and may be concentrically spaced around most of first transverse opening 211. A wall 215, which may be generally circular in cross-section, may be formed jointly by first transverse opening 211 and second transverse opening 213. A channel 217, which may fluidly couple the volumes defined by first transverse opening 211 and second transverse opening 213, may be provided in wall 215.

A first groove 231 may be provided in upper body 151. First groove 231, which may be formed in bottom surface 173 of upper body 151 (and which does not extend to top surface 171) may have a first end 233 fluidly connected to lower portion 185 of first counterbore 183 and a second end 235 fluidly connected to lower portion 195 of second counterbore 191. A second groove 241 may be provided in upper body 151. Second groove 241, which may be formed in bottom surface 173 of upper body 151 (and which does not extend to top surface 171) may have a first end 243 fluidly connected to lower portion 203 of third counterbore 199 and a second end 245 fluidly connected to lower portion 195 of second counterbore 191. A third groove 251, which may be formed in bottom surface 173 of upper body 151 (and which does not extend to top surface 171) may have a first end 253 fluidly connected to lower portion 195 of second counterbore 191 and a second end 255 fluidly connected to first transverse opening 211. A fourth groove 261, which may be formed in bottom surface 173 of upper body 151 (and which does not extend to top surface 171) may have a first end 263 fluidly connected to lower portion 209 of fourth counterbore 205 and a second end 265 fluidly connected to second transverse opening 213.

Figure 10A:
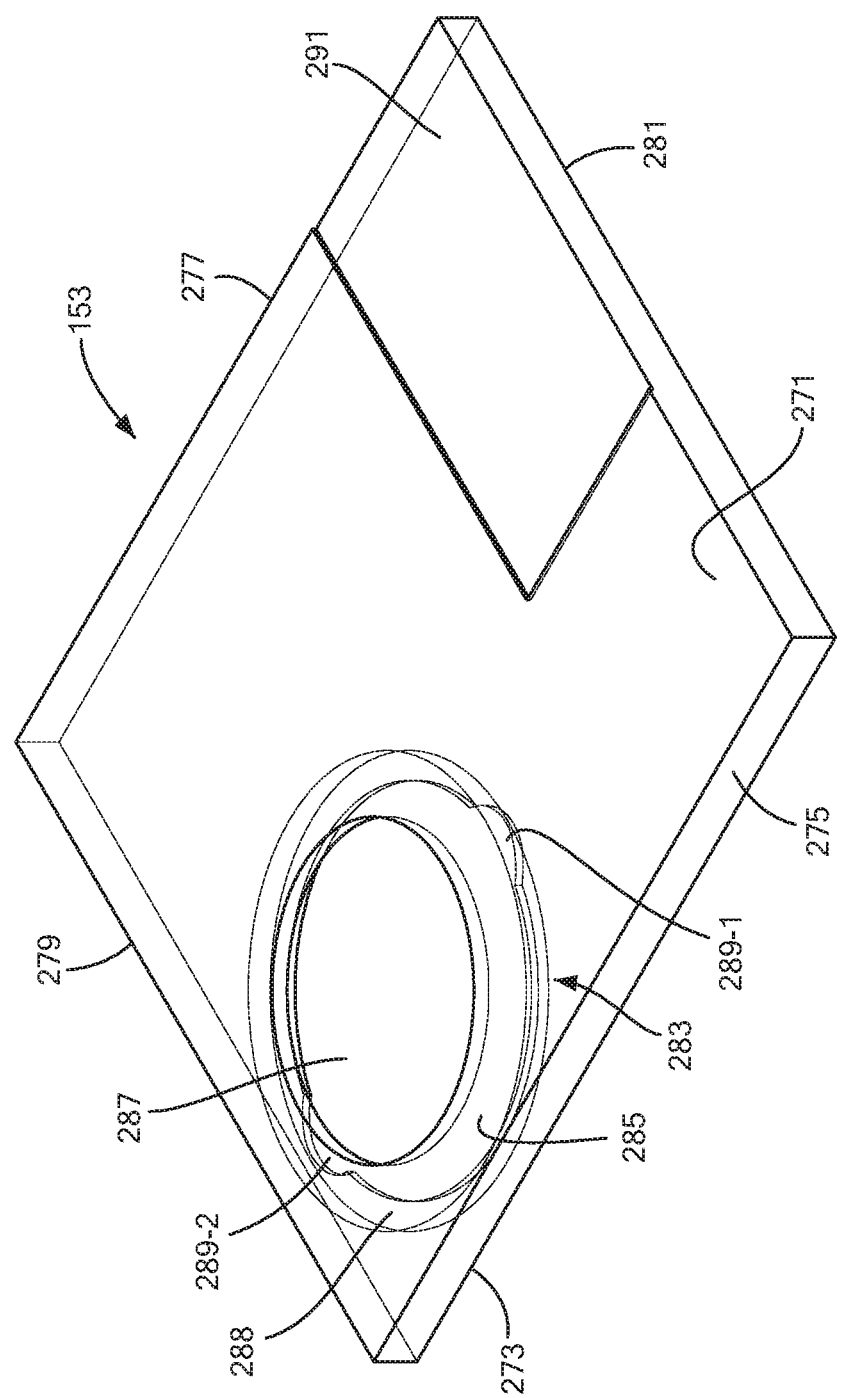
FIGS. 10(a) and 10(b) are top perspective and top views, respectively, of the lower layer of the analysis cartridge shown in FIG. 8(a)
Figure 10B:
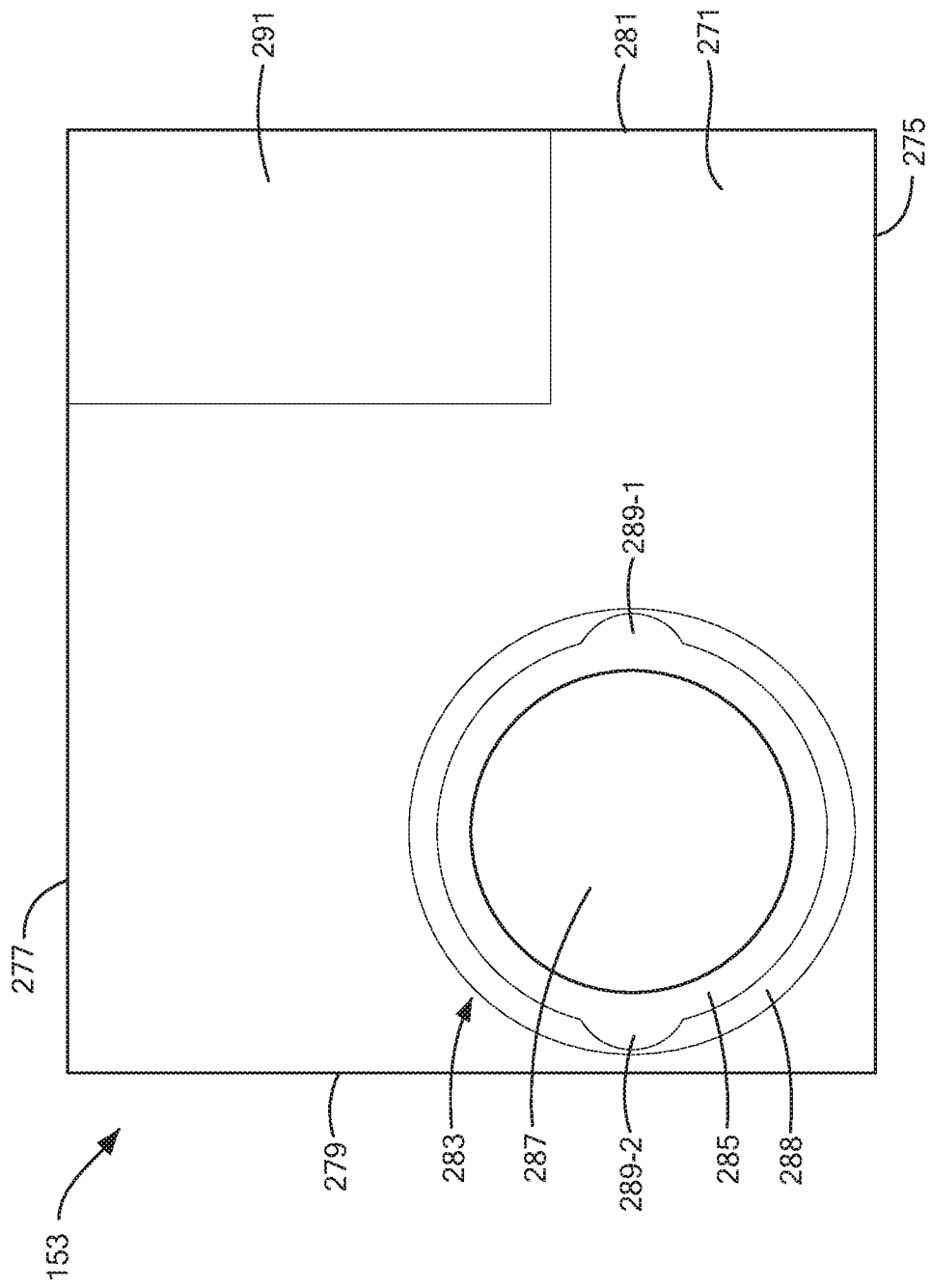

Lower body 153, which is also shown separately in FIGS. 10(a) and 10(b), may be a unitary (i.e., one-piece), generally rectangular, solid, planar structure made of a rigid, electrically non-conductive, chemically inert material, such as a suitable plastic or ceramic. In the present embodiment, lower body 153 is shown as being transparent or translucent, but it need not be. Lower body 153 may be shaped to include a top surface 271, a bottom surface 273, a front surface 275, a rear surface 277, a left side surface 279, and a right side surface 281. Top surface 271 of lower body 153 may be fixedly secured, by an adhesive or other suitable means, to bottom surface 173 of upper body 151, with front surface 275, rear surface 277, left side surface 279, and right side surface 281 of lower body 153 lying flush with front surface 175, rear surface 177, left side surface 179, and right side surface 181, respectively, of upper body 151. With lower body 153 thus mounted under upper body 151, grooves 231, 241, 251 and 261 have closed bottom surfaces defining microfluidic channels disposed between upper body 151 and lower body 153. Such microfluidic channels may be generally rectangular in cross-section and may have cross-sectional dimensions of 500 µm×100 µm.

Lower body 153 may be shaped to include a counterbore 283, which may be appropriately dimensioned to receive the combination of filter 73 and filter cap 75. Counterbore 283 may extend from top surface 271 to bottom surface 273 and may include a lower portion 285, an upper portion 287, and an intermediate portion 288, all of which may be of generally circular cross-section. Intermediate portion 288 may be of comparatively greater diameter and upper portion 287 may be of comparatively lesser diameter while lower portion 285 may be of intermediate diameter. Counterbore 283 of lower body 153 may be aligned with first counterbore 183 of upper body 151. Lower portion 285 of counterbore 283 may be shaped to include a pair of radially opposed recesses 289-1 and 289-2, which may be appropriately sized and shaped to receive side portions 103-1 and 103-2 of filter cap 75. In this manner, with filter 73 facing upwardly and with side portions 103-1 and 103-2 of filter cap 75 aligned with recesses 289-1 and 289-2, the combination of filter 73 and filter cap 75 may be inserted up through lower portion 285 of counterbore 283 and then may be secured in place by rotating filter cap 75 a quarter turn within intermediate portion 288 of counterbore 283.

Lower body 153 may also be shaped to include a recess 291 on top surface 271 for receiving sensor assembly 161. Recess 291 may have a thickness such that the top of sensor assembly 161 may lie flush with top surface 271 of lower body 153. Recess 291 may otherwise be dimensioned so that the front end of sensor assembly 161 may extend a short distance beyond front surface 275 of lower body 153.

As will be apparent from the discussion below, upper body 151 and lower body 153 may jointly form a support that may serve to hold and/or to support filter 73, filter 75, valve 155, first fluid pack 157, press 159, sensor assembly 161, and second fluid pack 163.

Figure 11A:
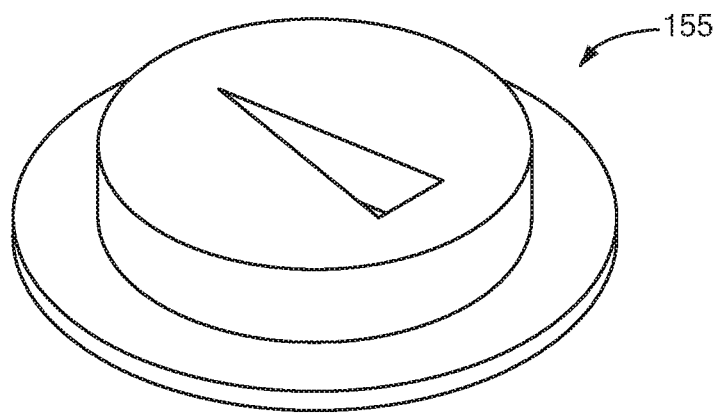
FIGS. 11(a) and 11(b) are enlarged top perspective and enlarged bottom views, respectively, of the valve of the analysis cartridge shown in FIG. 8(a)
Figure 11B:
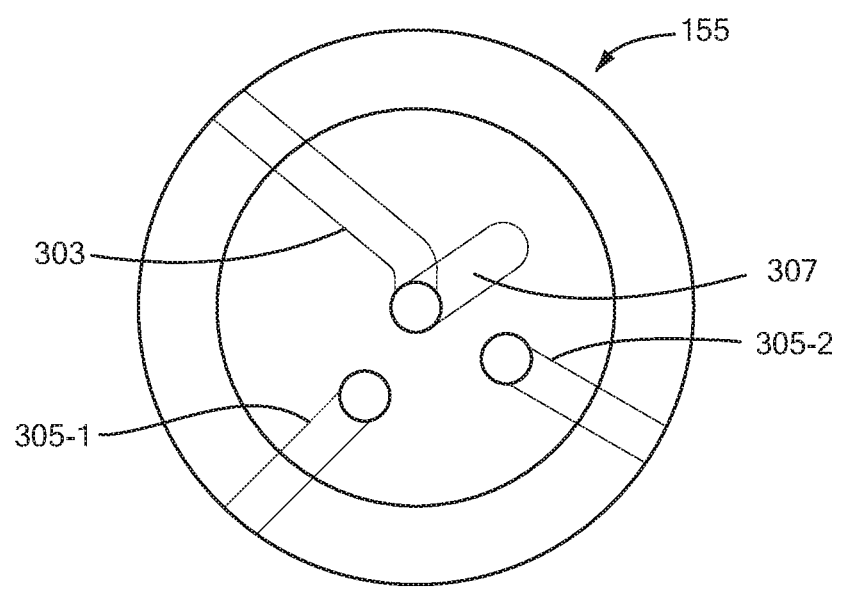

Valve 155, which is shown separately in FIGS. 11(a) and 11(b), may be mounted within second counterbore 191 of upper body 151. Valve 155 may be a rotary valve comprising an inlet channel 303, two outlet channels 305-1 and 305-2, and a rotary switch 307. Inlet channel 303 may be fluidly coupled to second end 235 of groove 231. Outlet channel 305-1 may be fluidly coupled to second end 245 of groove 241, and outlet channel 305-2 may be fluidly coupled to first end 253 of groove 251. When rotary switch 307 is placed in a first position (either manually or with a machine), inlet channel 303 and outlet channel 305-1 may be fluidly coupled to one another, and, when rotary switch 307 is placed in a second position (either manually or with a machine), inlet channel 303 and outlet channel 305-2 may be fluidly coupled to one another.

Figure 12A:
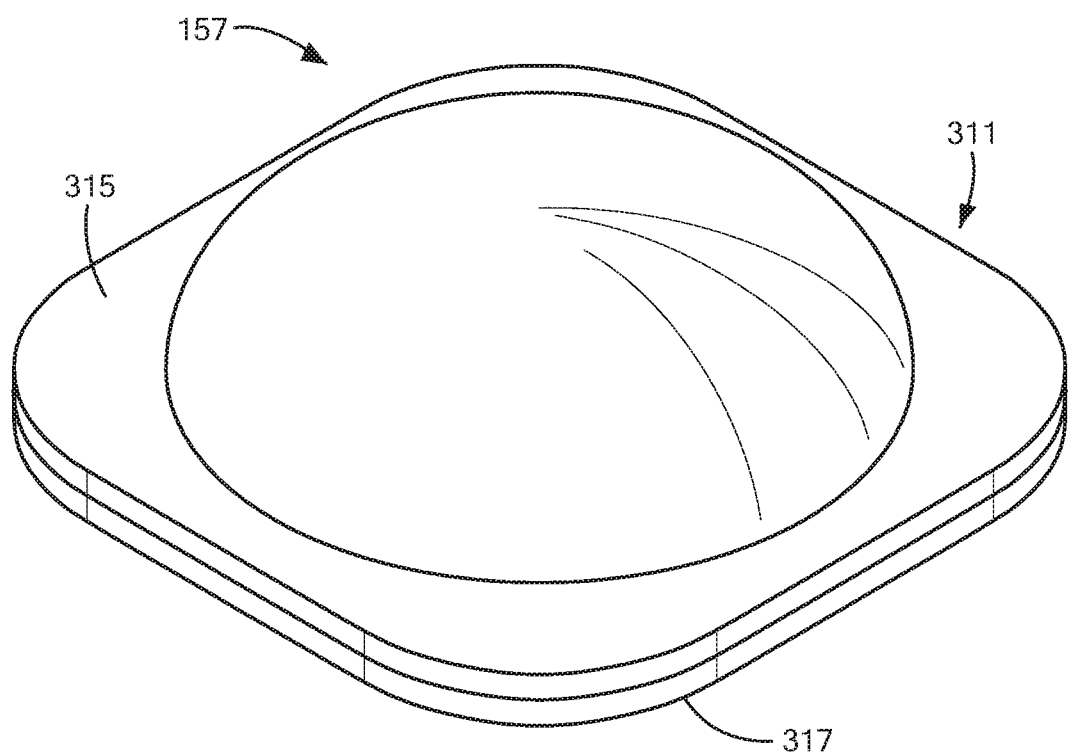
FIGS. 12(a) and 12(b) are enlarged perspective and enlarged section views, respectively, of the first fluid pack of the analysis cartridge shown in FIG. 8(a)
Figure 12B:
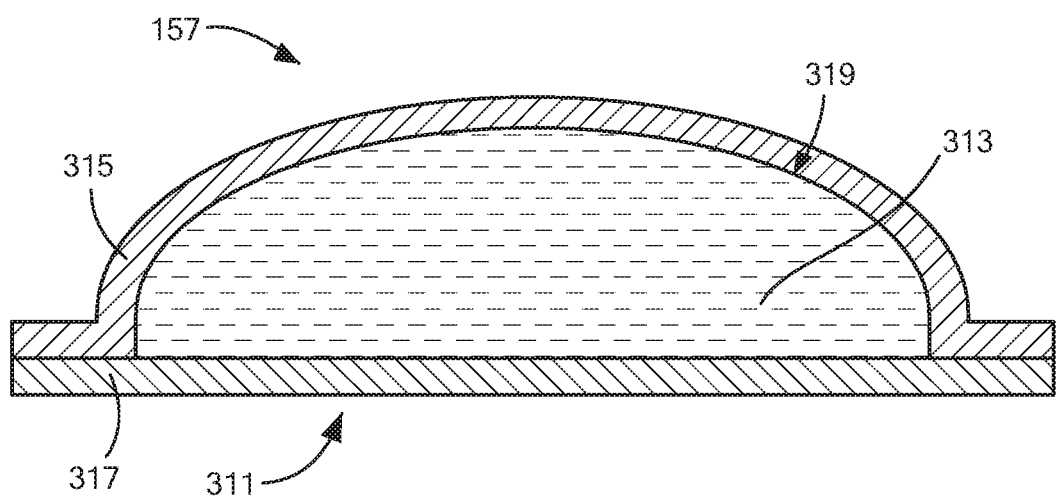

First fluid pack 157, which is also shown separately in FIGS. 12(a) and 12(b), may comprise a blister pouch 311 and a quantity of a fluid 313 disposed within blister pouch 311. Blister pouch 311, which may be conventional in construction, may comprise a first layer 315 and a second layer 317, wherein first layer 315 and second layer 317 may be fixedly joined together to form a cavity 319 therebetween. The periphery of second layer 317 of blister pouch 311 may be fixedly mounted, for example, by an adhesive or other suitable means, on top of the bottom surface of upper portion 201 of third counterbore 199. Second layer 317 of blister pouch 311 may be made of a material that may break in the central portion thereof when sufficient downward pressure is applied (either manually or with a machine) to first layer 315, thereby causing the contents of blister pouch 311 to flow into first end 243 of second groove 241.

Fluid 313 may be a fluid useful in eluting any THC from filter 73 and/or in helping to immobilize such THC on the working electrode of sensor assembly 161. Fluid 313 may comprise one or more alcohols and water in an alcohol/water ratio of 50/50 to 100/0 (v/v). Examples of suitable alcohols may comprise, but are not limited to, methanol, ethanol, 1-propanol, and isopropanol. Fluid 313 may further comprise a surfactant, such as, but not limited to, sodium docusate, TWEEN® 20 polyethylene glycol sorbitan monolaurate, TWEEN® 40 polyoxyethylenesorbitan monopalmitate, TRITON X-100 polyethylene glycol tert-octylphenyl ether, tetradecyltrimethylammonium bromide, SURFYNOL® 420 ethoxylated acetylenic surfactant, SURFYNOL® 480 ethoxylated acetylenic surfactant, SILWET 68 organomodified siloxane, and PLURACARE 1307® Ethylenediamine alkoxlate block copolymer. The surfactant may be present in fluid 313 in a concentration range of about 0-5% (w/v). The total volume of fluid 313 in blister pouch 311 may be in the range of approximately 50-100 µl.

Figure 13:
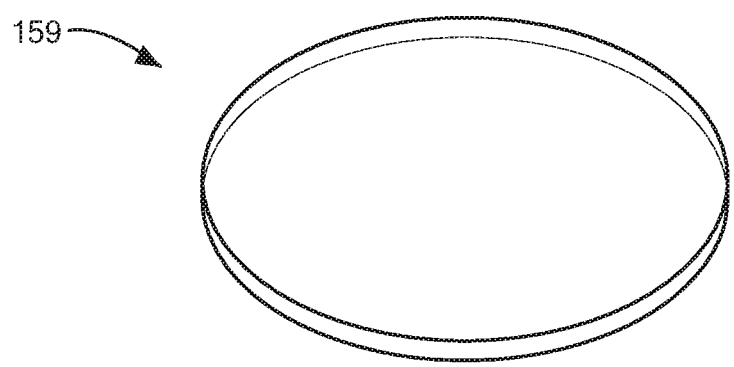
FIG. 13 is an enlarged perspective view of the press of the analysis cartridge shown in FIG. 8(a)

Press 159, which is also shown separately in FIG. 13, may be a unitary (i.e., one-piece), solid, disc-shaped structure made of a flexible, electrically non-conductive, chemically inert material, such as a suitable plastic or rubber. Although shown as transparent in the present embodiment, press 159 need not be transparent. Press 159 may be movably mounted in lower portion 185 of first counterbore 183 of upper body 151. In this manner, by applying downward pressure to press 159 (either by inserting one or more fingers or a tool downwardly through upper portion 187), press 159 may be moved downwardly towards filter cap 75. Because filter cap 75 is mounted in lower body 153 so as to be axially stationary while press 159 is moved downwardly, such downward pressure applied to press 159 may be used to squeeze filter 73 between press 159 and filter cap 75. A nonporous film or cover (not shown) may be adhered or otherwise secured to the bottom surface of filter cap 75 when filter cap 75 is mounted within lower body 153 so that, when filter 73 is squeezed in the above-described manner, matter expelled from filter 73 may not exit through the bottom of 285 of counterbore 283, but rather, may pass into groove 231.

Figure 14:
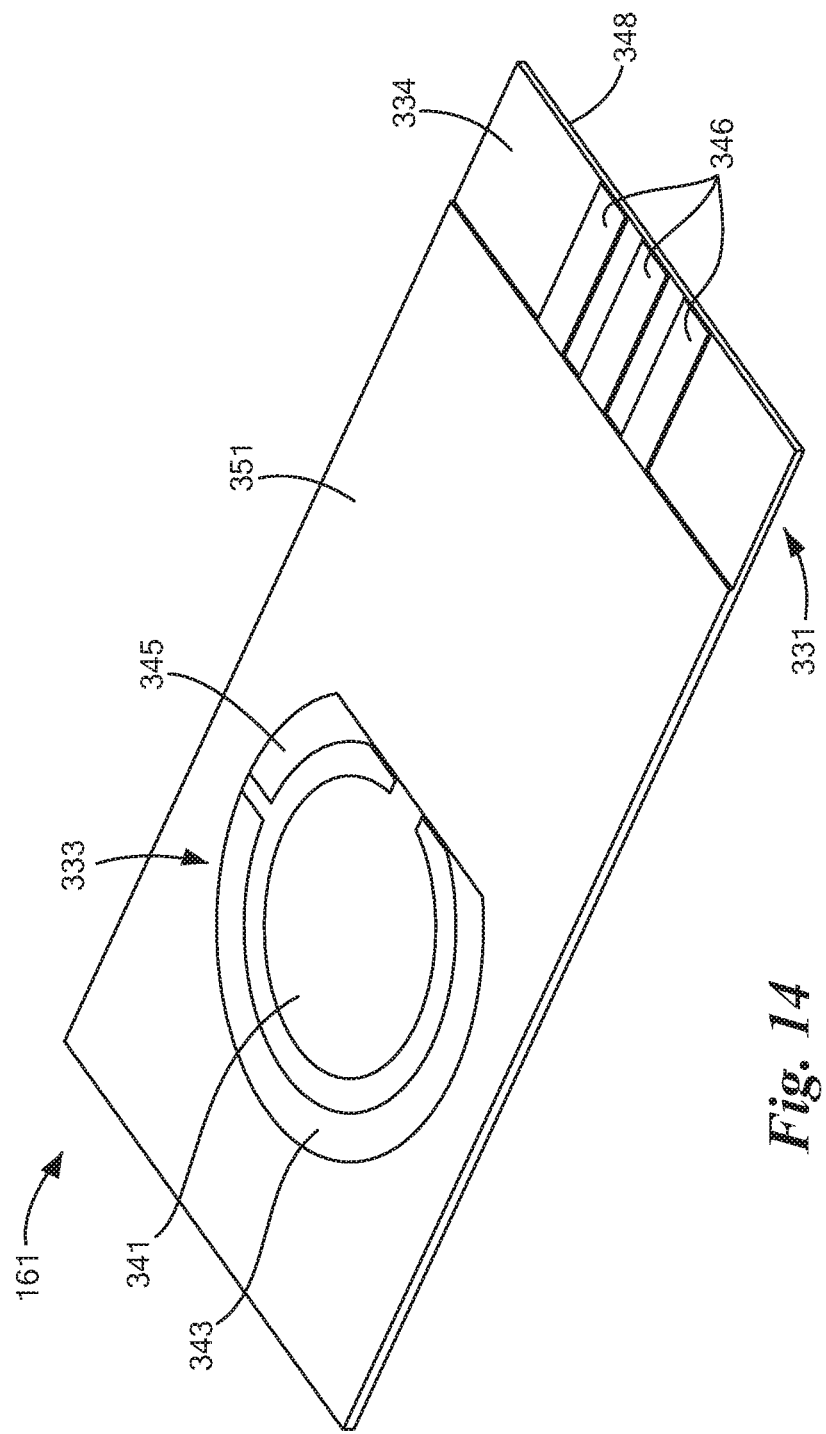
FIG. 14 is an enlarged perspective view of the sensor assembly of the analysis cartridge shown in FIG. 8(a)

Sensor assembly 161, which is also shown in separately in FIG. 14, may comprise a substrate 331. Substrate 331 may be a generally rectangular, planar structure made of a rigid, electrically non-conductive, chemically inert material, such as a suitable plastic or ceramic. Sensor assembly 161 may further comprise an electrochemical sensing element 333, which may be disposed on a top surface 334 of substrate 331. Electrochemical sensing element 333 may comprise a working electrode 341, a counter electrode 343, and a reference electrode 345. Each of working electrode 341, counter electrode 343, and reference electrode 345 may be formed by screen-printing a suitable ink on top surface 334 of substrate 331. For example, each of working electrode 341 and counter electrode 343 may be formed by screen printing a carbon ink on substrate 331, and reference electrode 345 may be formed by screen printing a silver ink on substrate 331. Working electrode 341 may comprise a generally circular structure. Counter electrode 343 may comprise an arcuate structure spaced concentrically around a first portion of working electrode 341, and reference electrode 345 may comprise an arcuate structure spaced concentrically around a second portion of working electrode 341. Each of working electrode 341, counter electrode 343, and reference electrode 345 may have a conductive track 346 on top surface 334 that takes its respective electrode to a rear edge 348 of substrate 331.

Sensor assembly 161 may further comprise an insulation layer 351. Insulation layer 351 may comprise an electrically non-conductive, chemically inert material, such as a suitable plastic or ceramic. Insulation layer 351 may be positioned over substantially the entirety of top surface 334 of substrate 331, except in the areas of working electrode 341, counter electrode 343, and reference electrode 345 and in the area proximate to rear edge 348 of substrate 331 encompassing tracks 346.

One distinction of sensor assembly 161, as compared to sensor assemblies of other THC-detection methods and systems, is that sensor assembly 161 does not require the use of any specialized coatings on its electrodes and, instead, may comprise unmodified electrodes. Notwithstanding the above, the electrodes may be treated with various coatings to control surface hydrophobicity, conductivity, and wettability and, thus, (1) aid with the macroscale dispersion and diffusion of the sample on the electrode surface, (2) improve the adsorption of THC molecules on the microporous electrode surface and increase their availability to be oxidized during the voltammetry measurement, and (3) enhance electron transfer and increase sensitivity.

Sensor assembly 161 may be fixedly mounted, for example, using an adhesive or other suitable means, on top of recess 291 of lower body 153. With sensor assembly 161 thus mounted, working electrode 341 may be aligned with first transverse opening 211 of upper body 151, and counter electrode 343 and reference electrode 345 may be aligned with second transverse opening 213 of upper body 151. Rear edge 348 of substrate 331 may extend rearwardly a short distance beyond the respective rear surfaces of upper body 151 and lower body 153 to facilitate the interfacing of sensor assembly 161 with reader 17.

Figure 15A:
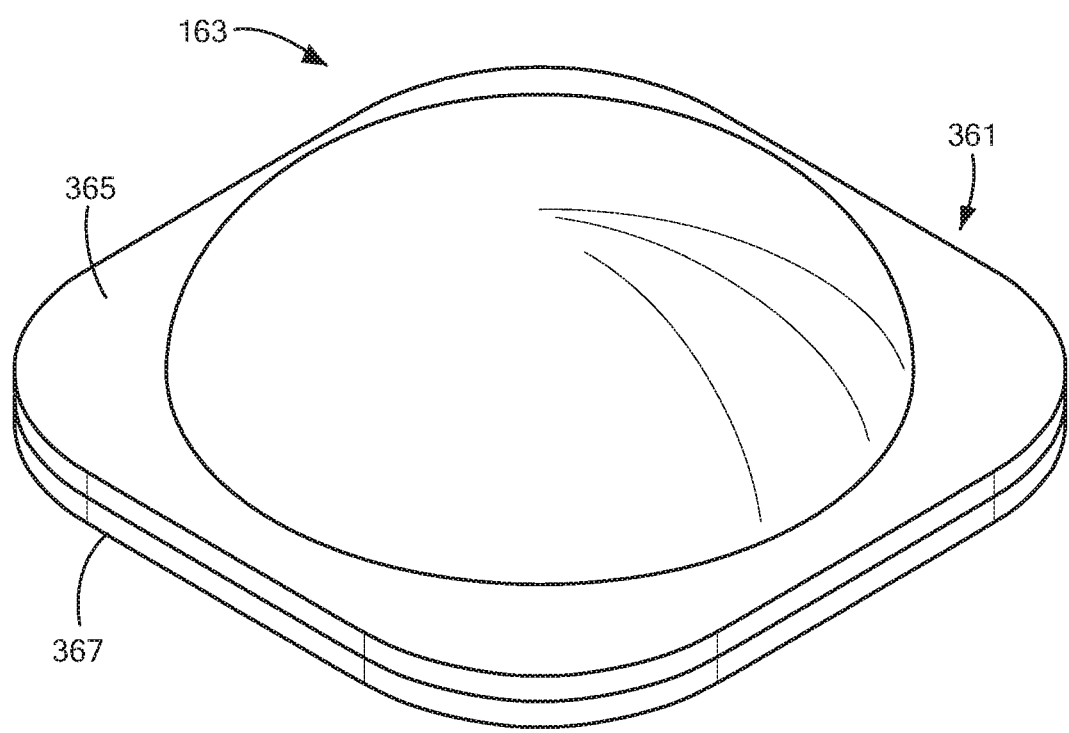
FIGS. 15(a) and 15(b) are enlarged perspective and enlarged section views, respectively, of the second fluid pack of the analysis cartridge shown in FIG. 8(a)
Figure 15B:
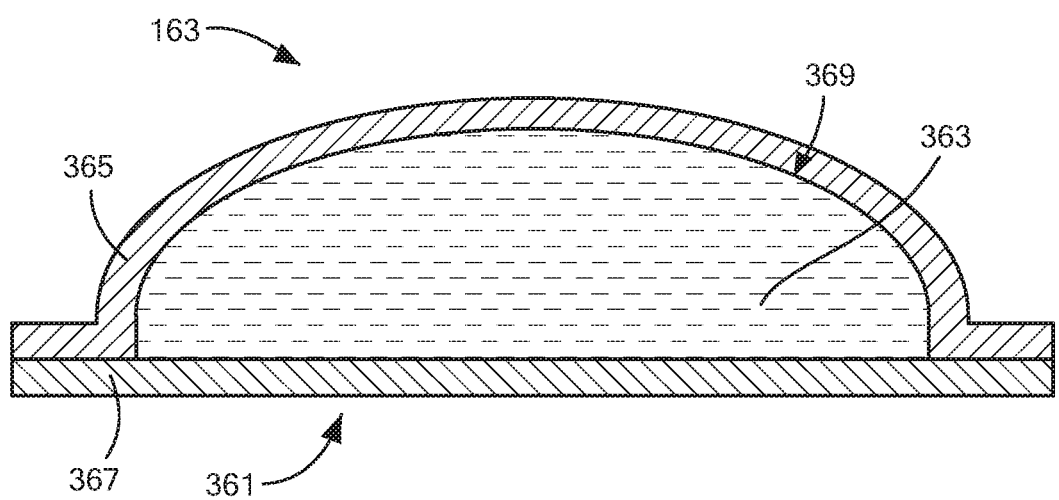

Second fluid pack 163, which is also shown separately in FIGS. 15(a) and 15(b), may comprise a blister pouch 361 and a quantity of a fluid 363 disposed within blister pouch 361. Blister pouch 361, which may be similar to blister pouch 311 of first fluid pack 157, may comprise a first layer 365 and a second layer 367, wherein first layer 365 and second layer 367 may be fixedly joined together to form a cavity 369 therebetween. The periphery of second layer 367 of blister pouch 361 may be fixedly mounted, for example, by an adhesive or other suitable means, on top of the bottom surface of upper portion 207 of fourth counterbore 205. Second layer 367 of blister pouch 361 may be made of a material that may break in the central portion thereof when sufficient downward pressure is applied (either manually or with a machine) to first layer 365, thereby causing the contents of blister pouch 361 to flow into first end 263 of fourth groove 261.

Fluid 363 may be a solution useful in enabling the performance of an electrochemical analysis of the sample. To this end, fluid 363 may consist of or may comprise one or more electrolytic solutions, such as, but not limited to, one or more aqueous electrolytic solutions. Suitable aqueous electrolytic solutions may include, but are not limited to, solutions of NaOH, KOH, and borate buffer solutions with a pH in the range of 10-14. The quantity of fluid 363 in blister pouch 311 may be in the range of approximately 200 µl to 600 µl.

Figure 16:
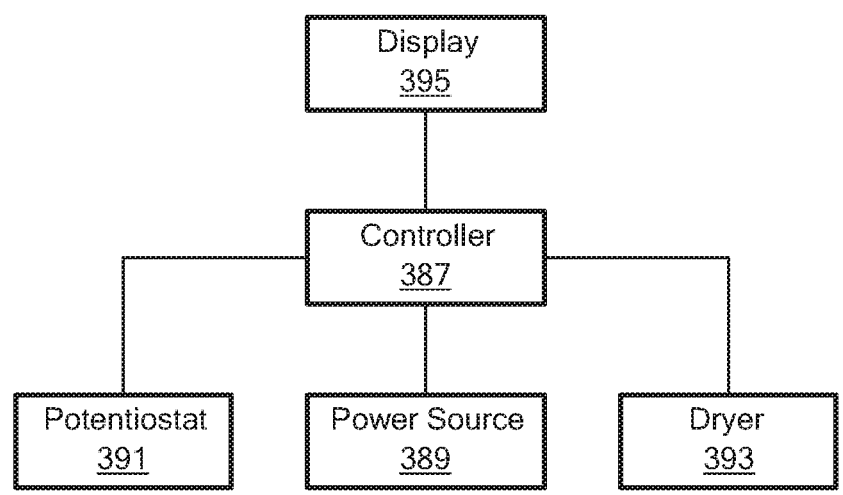
FIG. 16 is a simplified schematic of the electronic components of the reader shown in FIG. 1.

Referring back now to FIG. 1, reader 17 may comprise a container 383. Container 383, in turn, may comprise a slidably mounted drawer 385, into which cartridge 15, may be removably mounted in order to interface with at least some of the componentry of reader 17. Referring now to FIG. 16, the componentry of reader 17 is schematically shown. As can be seen, reader 17 may comprise a controller 387, a power source 389, a potentiostat 391, a dryer 393, and a display 395. Controller 387 may comprise a conventional computer processor or the like and may be equipped with suitable software for controlling its operation. Power source 389, which is electrically connected to controller 387, may comprise a battery or other portable source of electricity. Where power source 389 is a battery, such a battery may be, for example, a 12 V DC battery that can be recharged through a USB connection. Potentiostat 391 may be electrically coupled to controller 387 and may be positioned within container 383 so that, when cartridge 15 is positioned within drawer 385 and drawer 385 is pushed into container 383, potentiostat 391 may be operatively connected to electrochemical sensing element 333 in such a way that, when desired, an electrochemical analysis of a sample may be performed. Dryer 393, which may comprise a heater, an air blower, a vacuum, or a combination thereof, may be electrically coupled to controller 387 for selective actuation and may be positioned within container 383 to dry fluid 313 that has been deposited on working electrode 341. Display 395 may be electrically coupled to controller 387 and may be mounted on or within an opening of container 383 in such a way that it may easily be viewed. Display 395 may be used to display operating instructions for system 11 and/or to display the results of any electrochemical analysis performed using potentiostat 391.

Collection device 13, which may be designed to be a disposable, single-use item, may be maintained in an assembled and sterile condition prior to use. Analysis cartridge 15, which may be designed to be a disposable, single-use item, may be maintained in an assembled and sterile condition prior to use. Reader 17, which may be designed to be a portable, multi-use item, may be cleaned, reconditioned and/or reset between uses.

Figure 17:
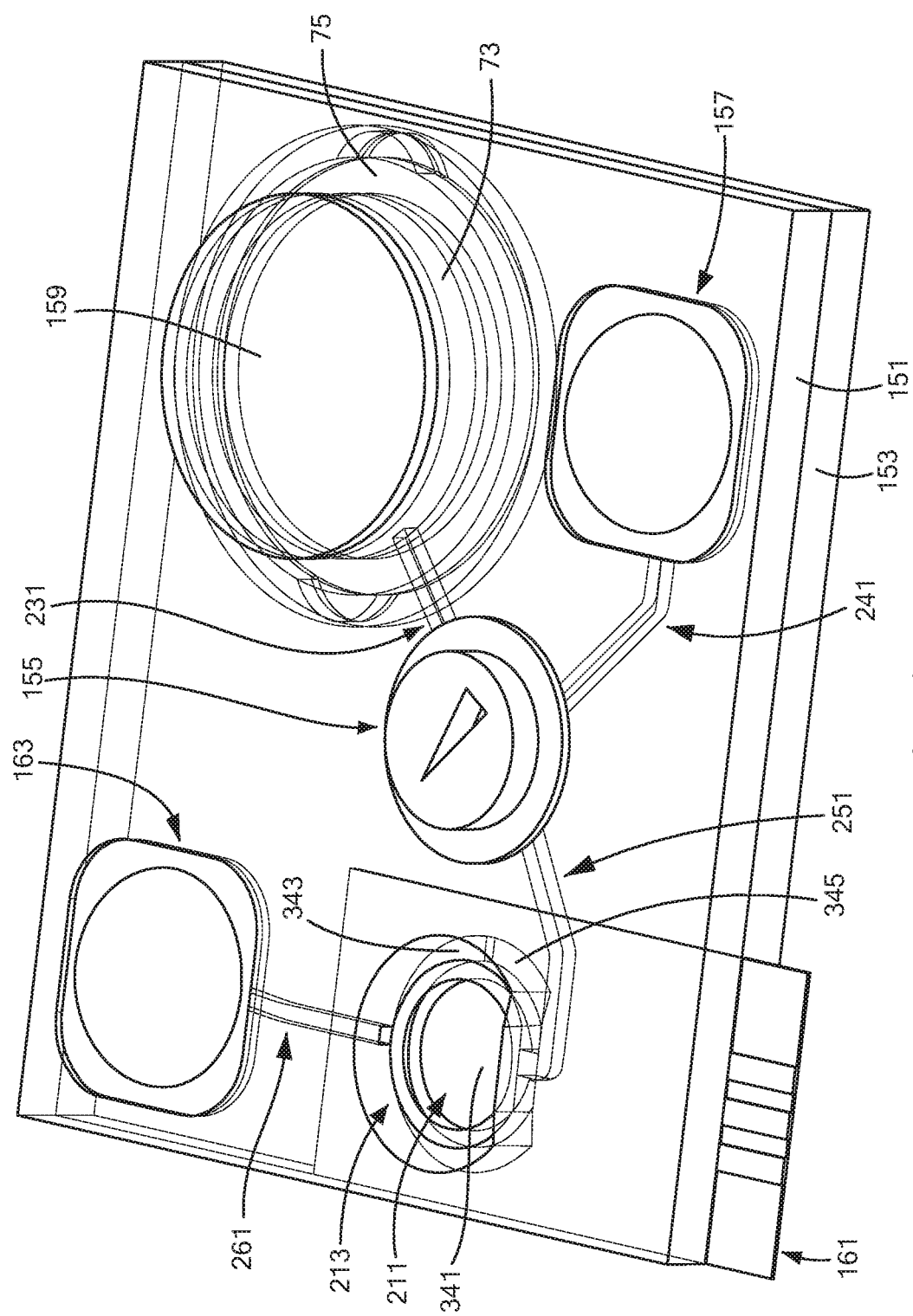
FIG. 17 is a top perspective view showing the analysis cartridge of FIG. 8(a), with the filter and the filter cap of FIG. 7 installed therein.

In use, proximal end 61 of first tubular portion 55 of mouthpiece 23 may be inserted into a subject's mouth, and the subject may then exhale into mouthpiece 23 until such time as inflatable receptacle 25 may be fully inflated. This may involve exhalation into mouthpiece 23 for a period of time on the order of up to a couple of minutes or longer. Next, latch 53 may be uncoupled from filter assembly 25, and filter assembly 25 may then be removed from body 21. Next, the combination of filter 73 and filter cap 75 may be detached from holder 71, and the combination of filter 73 and filter cap 75 may be coupled to analysis cartridge 15 by being inserted up into counterbore 283 and then rotated a quarter turn (see FIG. 17).

Next, with rotary switch 307 of valve 155 positioned so as to couple inlet channel 303 to outlet channel 305-1, sufficient downward pressure may be applied to first fluid pack 157 so as to cause blister pouch 311 to burst, causing fluid 313 to exit from blister pouch 311, to pass through groove 241, valve 155, and groove 231, and to be imbibed by filter 73. With filter 73 thus imbibed with fluid 313, cartridge 15 may then be gently shaken or agitated so that any THC present within filter 73 may be eluted therefrom, together with fluid 313.

Next, rotary switch 307 of valve 155 may be positioned so that inlet channel 303 is coupled to outlet channel 305-2. Then, sufficient downward pressure may be applied to press 159 so as to cause filter 73 to be squeezed between press 159 and filter cap 75. The squeezing of filter 73 causes fluid 313, together with any eluted THC or other eluted substances, to flow from filter 73, to pass through groove 231, valve 155, and groove 251, and to enter transverse opening 211, whereupon fluid 313 may disperse over working electrode 341. Wall 215 may prevent fluid 313 from spreading out to counter electrode 343 and/or reference electrode 345.

Next, fluid 313 present within transverse opening 211 may be dried, whereby any THC present within fluid 313 may be immobilized on working electrode 341. Such drying may be effected simply by allowing cartridge 15 to air-dry or may be expedited by the application of heat, suction, blown air or a combination thereof to the space filling transverse opening 211. Where heat, suction and/or blown air is used for drying, such heat, suction and/or blown air may be provided by a heater, a vacuum and/or a fan provided in reader 17, with cartridge 15 being inserted into reader 17 for drying.

Next, sufficient downward pressure may be applied to second fluid pack 163 so as to cause blister pouch 361 to burst, causing fluid 363 to flow from blister pouch 361 through groove 261 and to enter transverse opening 213, whereupon fluid 363 may disperse over counter electrode 343 and reference electrode 345. In addition, a portion of fluid 363 may pass from transverse opening 213 through channel 217 to transverse opening 213, whereupon said portion of fluid 363 may disperse over working electrode 341.

Figure 18:
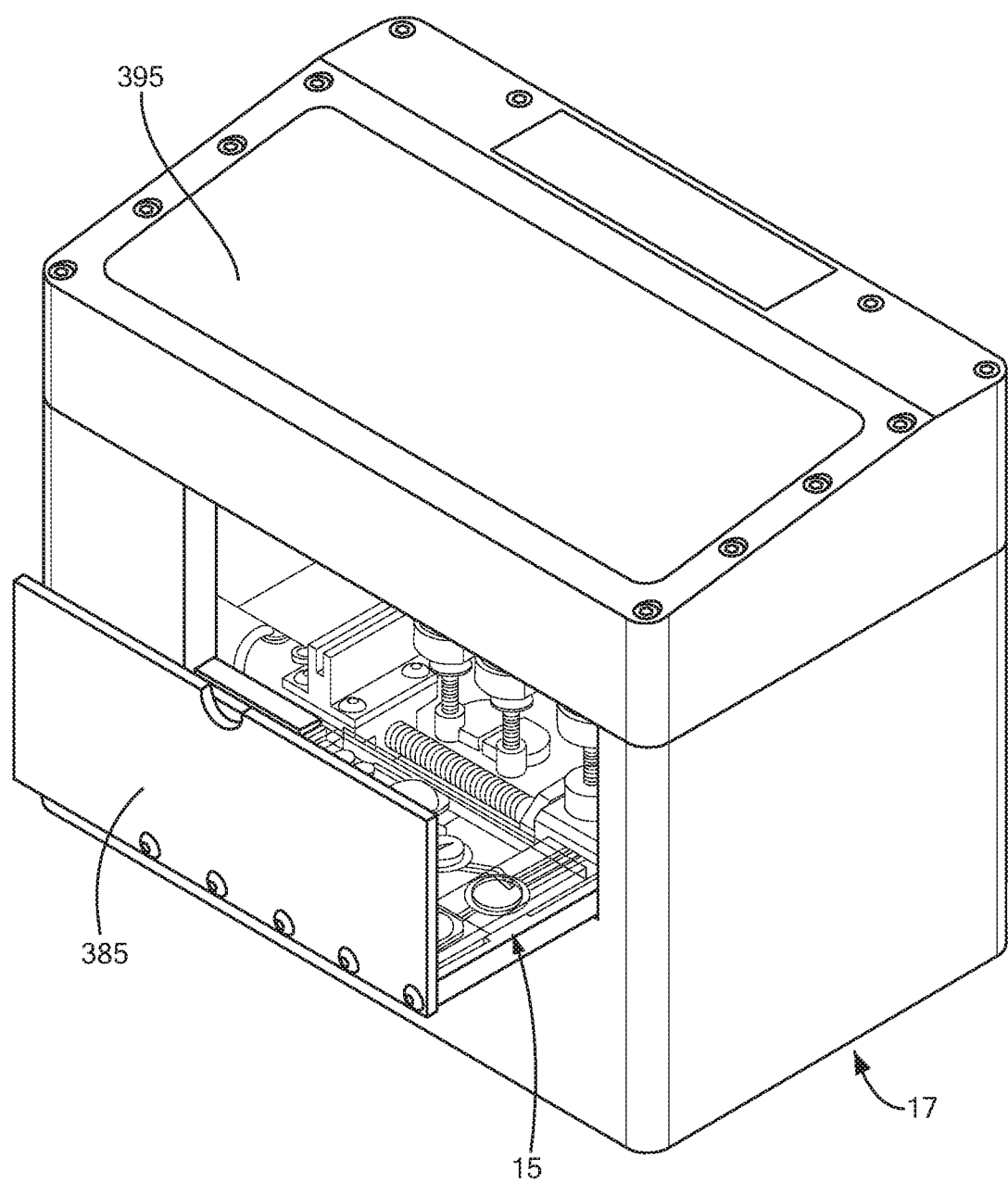
FIG. 18 is a top perspective view showing the analysis cartridge of FIG. 17 seated within the drawer of the reader of FIG. 1.

Next, one may insert cartridge 15, together with filter 73 and filter cap 75, into drawer 385 of reader 17 (see FIG. 18) and may close drawer 385 so that leads from potentiostat 391 may interface with sensor assembly 161. Then, reader 17 may be used to electrochemically analyze the sample. This may involve, for example, using a pulse voltammetry technique, such as, but not limited to, square-wave voltammetry and differential pulse adsorption voltammetry. Of these techniques, square-wave voltammetry may be preferred. According to this technique, a pulse waveform is applied and scanned consisting of regular pulses superimposed on a positive potential ramp with a linear scan rate (mV/sec) to oxidize accumulated THC on the sensor surface. For example, the settings for square-wave voltammetry may include 200 mV amplitude, 7 step potential and 7 Hz frequency.

Using this technique, the current signal results from electron transfer and is proportional to the amount of THC, thus allowing trace analysis of THC on the sensor surface. The results obtained may then be compared to appropriate standards to quantify the amount of THC. One distinction of the above-described technique, as compared to many existing techniques, is that the present technique involves the direct electrochemical detection of THC, via oxidation of the hydroxyl group of THC, as opposed to the indirect electrochemical detection of THC by detecting a compound that reacts with THC.

It should be understood that many of the steps described above that involve the manipulation of cartridge 15 may be performed either manually or using a machine. In addition, it should be understood that reader 17 may be constructed to perform some or all of such manipulations automatically.

It should also be understood that, although system 11 permits an advantageous implementation of the method of the present invention, the method of the present invention need not be performed using system 11.

It should further be understood that, although the method and the system of the present invention have been described herein in the context of the detection and/or quantification of THC, the method and the system of the present invention is not limited to the detection and/or quantification of THC and may be used to detect and/or to quantify other types of analytes, such as, but not limited to, other types of organic compounds with a phenolic group. Moreover, as noted above, although the present invention is often described herein in the context of detecting and/or quantifying THC or other analytes in exhaled breath, the present invention is not to be limited to detecting and/or quantifying THC or other analytes in exhaled breath and could be used to detect and/or to quantify THC or other analytes in other types of fluid samples.

Lastly, some benefits and features that apply to one or more embodiments of the present invention include the following:

- The present invention advances the direct electrochemical detection of THC with short response time and high sensitivity in a controllable simple system that does not involve the complexity of measurement using biomolecule labels with elaborate amplification steps.
- The present invention provides a portable, cost-effective and non-invasive electrochemical sensor device for near real-time exhaled breath THC detection to be used at roadside for drivers. This will eliminate the need for expensive and time-consuming analytical techniques which have a turnaround time of several days.
- The invention demonstrates the feasibility of single step THC detection in aqueous solutions using disposable screen-printed electrodes.
- The invention successfully establishes a new electrochemical methodology for THC measurement by applying a proprietary procedure for non-electrolytic pre-concentration of the THC on an electrode surface, followed by detection and quantification using a combination of pulse voltammetry techniques. The approach uses physical convection, van der Wall forces, hydrophobic interactions and vacuum assisted thermal adsorption to concentrate THC to the electrode surface.
- Using the present invention, there is a limit of detection of 1 ng.
- The present invention allows the generation of 1 µA of peak current with only 1.07 ng/mL THC, as all of the THC in solution is deposited on the working electrode.
- The present invention represents an advancement over existing THC detection techniques since, with existing techniques, it is difficult to measure THC in exhaled breath, considering that the THC is released as aerosol particles and is not dissolved in water.
- Volatile breath constituents (such as propyl alcohol, isopropyl alcohol, ethyl acetate, acetone, etc.) will not cause any issues with the present technique. Moreover, similar electrochemical analysis performed on saliva samples containing potentially interfering substances, such as thymol (found in mouthwash), eugenol (found in cloves, clove cigarettes), epigallocatechin gallate (EGCG) (found in green tea), capsaicin (found in spicy food) and tobacco smoke, showed less than 5% false signal at the THC oxidation potential, except for eugenol, which was only 12%. (The concentration of tested interferent was for equal mass concentration.)

The embodiments of the present invention described above are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A method for detecting and/or quantifying $\Delta^9$-tetrahydrocannibinol (THC) in exhaled breath, the method comprising the steps of:
   (a) providing an electrochemical sensing element;
   (b) providing a filter that traps THC in exhaled breath;
   (c) causing a subject to exhale onto the filter, whereby at least some of the THC, if present in an exhaled breath, is trapped in the filter;
   (d) washing the filter with an eluent, whereby at least some of the THC trapped in the filter is eluted therefrom in an eluate;
   (e) depositing the eluate from the filter onto the electrochemical sensing element;
   (f) drying the eluate on the electrochemical sensing element, whereby at least some of the THC in the eluate is immobilized on the electrochemical sensing element; and
   (g) directly electrochemically detecting and/or quantifying the immobilized THC, wherein said detecting and/or quantifying step comprises performing a pulse voltammetry technique to obtain a measurement and comparing said measurement to a standard and wherein said pulse voltammetry technique is performed in the presence of an aqueous alkaline electrolyte.

2. The method as claimed in claim 1 wherein the electrochemical sensing element comprises a working electrode, a counter electrode, and a reference electrode.

3. The method as claimed in claim 2 wherein the working electrode, the counter electrode, and the reference electrode are screen-printed electrodes on a substrate.

4. The method as claimed in claim 3 wherein the screen-printed electrodes are devoid of surface treatment.

5. The method as claimed in claim 1 wherein said drying step comprises using a vacuum.

6. The method as claimed in claim 1 wherein said drying step comprises using a heater.

7. The method as claimed in claim 1 wherein said drying step comprises using an air blower.

8. The method as claimed in claim 1 wherein said drying step comprises air-drying the deposited eluate.

9. The method as claimed in claim 1 wherein said pulse voltammetry technique comprises square-wave voltammetry.

10. The method as claimed in claim 1 wherein said pulse voltammetry technique comprises differential pulse anodic voltammetry.

11. The method as claimed in claim 10 wherein at least one of steps (c), (d), (e), (f), and (g) is automated.

12. The method as claimed in claim 10 further comprising the step of displaying a result of step (g).

13. The method as claimed in claim 10 wherein the eluent comprises at least one alcohol.

14. The method as claimed in claim 13 wherein the at least one alcohol comprises at least one member selected from the group consisting of methanol, ethanol, 1-propanol, and isopropanol.

15. The method as claimed in claim 14 wherein the eluent further comprises water.

16. A method for detecting and/or quantifying $\Delta^9$-tetrahydrocannibinol (THC) in exhaled breath, the method comprising the steps of:
   (a) providing an electrochemical sensing element;
   (b) providing a filter that traps THC in exhaled breath;

(c) causing a subject to exhale onto the filter, whereby at least some of the THC, if present in an exhaled breath, is trapped in the filter;

(d) washing the filter with an eluent, wherein the eluent comprises at least one alcohol, wherein the at least one alcohol comprises at least one member selected from the group consisting of methanol, ethanol, 1-propanol, and isopropanol, and wherein the eluent further comprises a surfactant, whereby at least some of the THC trapped in the filter is eluted therefrom in an eluate;

(e) depositing the eluate from the filter onto the electrochemical sensing element;

(f) drying the eluate on the electrochemical sensing element, whereby at least some of the THC in the eluate is immobilized on the electrochemical sensing element; and (g) directly electrochemically detecting and/or quantifying the immobilized THC.

17. A system for use in detecting and/or quantifying $\Delta^9$-tetrahydrocannibinol (THC) in exhaled breath, the system comprising:

(a) a collection device, the collection device comprising a filter that traps THC in exhaled breath;

(b) an analysis cartridge, the analysis cartridge comprising
   (i) a support, the support comprising a receptacle for receiving the filter from the collection device,
   (ii) an electrochemical sensing element coupled to the support, the electrochemical sensing element comprising a working electrode,
   (iii) a quantity of an eluent solution associated with the support for use in eluting THC from the filter in an eluate deposited onto the working electrode,
   (iv) a quantity of an electrolytic solution associated with the support for use in performing an electrochemical analysis, and (c) a reader, the reader adapted to be electrically coupled to the electrochemical sensing element and comprising a potentiostat and a controller for directly determining the presence and/or quantity of THC on the working electrode.

18. The system as claimed in claim 17 wherein the collection device further comprises a filter holder and wherein the filter is removably mounted in the filter holder.

19. The system as claimed in claim 18 wherein the collection device further comprises a filter cap and wherein the filter cap is removably mounted on the filter holder, with the filter being positioned sandwiched between the filter holder and the filter cap.

20. The system as claimed in claim 18 wherein the collection device further comprises a body, the body having a fluid channel, and wherein the filter holder is removably mounted in the body, with the filter in fluid communication with the fluid channel of the body.

21. The system as claimed in claim 17 wherein the reader further comprises a container, the container comprising a drawer onto which the analysis cartridge may be removably seated.

22. The system as claimed in claim 21 wherein the reader further comprises a dryer for drying the eluate.

23. The system as claimed in claim 22 wherein the dryer comprises at least one of a heater, a vacuum, and an air blower.

24. The system as claimed in claim 23 wherein the reader further comprises a display for displaying a result of the determination of the presence and/or quantity of THC on the working electrode.

25. An analysis cartridge for use in determining the presence or quantity of $\Delta^9$-tetrahydrocannibinol (THC) in a fluid sample, the analysis cartridge comprising:

(a) a support, the support comprising a receptacle for receiving a filter;

(b) a press movably mounted in the receptacle for use in applying pressure to the filter;

(c) an electrochemical sensing element coupled to the support, the electrochemical sensing element comprising a working electrode;

(d) a first fluid pack, the first fluid pack being coupled to the support and comprising a quantity of an eluent solution;

(e) a second fluid pack, the second fluid pack being coupled to the support and comprising a quantity of an electrolytic solution;

(f) a valve, the valve coupled to the support;

(g) a first fluid conduit in the support for use in fluidly coupling the receptacle to the valve;

(h) a second fluid conduit in the support for use in fluidly coupling the first fluid pack to the valve;

(i) a third fluid conduit in the support for use in fluidly coupling the valve to a first space directly above the electrochemical sensing element; and (j) a fourth fluid conduit in the support for use in fluidly coupling the second fluid pack to a second space directly above the electrochemical sensing element.

* * * * *